(12) United States Patent
Ryu et al.

(10) Patent No.: US 8,209,010 B2
(45) Date of Patent: Jun. 26, 2012

(54) SYSTEMS AND METHODS FOR OPTIMIZING MULTI-SITE CARDIAC PACING AND SENSING CONFIGURATIONS FOR USE WITH AN IMPLANTABLE MEDICAL DEVICE

(75) Inventors: Kyungmoo Ryu, Palmdale, CA (US);
Stuart Rosenberg, Castaic, CA (US);
Allen Keel, San Francisco, CA (US);
Taraneh Ghaffari Farazi, Santa Clara, CA (US); Xiaoyi Min, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 277 days.

(21) Appl. No.: 12/703,069

(22) Filed: Feb. 9, 2010

(65) Prior Publication Data
US 2011/0196441 A1 Aug. 11, 2011

(51) Int. Cl.
*A61N 1/00* (2006.01)

(52) U.S. Cl. .................. 607/9; 607/16; 607/62
(58) Field of Classification Search .............. 600/300, 600/301, 508–521; 607/2, 9–28, 62
See application file for complete search history.

(56) References Cited

U.S. PATENT DOCUMENTS 6,409,664 B1 * 6/2002 Kattan et al. .................. 600/300
* cited by examiner

*Primary Examiner* — Scott Getzow

(57) ABSTRACT

Techniques are provided for use with an implantable cardiac stimulation device equipped for multi-site left ventricular (MSLV) pacing using a multi-pole LV lead. In one example, referred to herein as QuickStim, cardiac pacing configurations are optimized based on an assessment of hemodynamic benefit and device longevity. In another example, referred to herein as QuickSense, cardiac sensing configurations are optimized based on sensing profiles input by a clinician. Various virtual sensing channels are also described that provide for the multiplexing or gating of sensed signals. Anisotropic oversampling is also described.

2 Claims, 16 Drawing Sheets

US 8,209,010 B2

SYSTEMS AND METHODS FOR OPTIMIZING MULTI-SITE CARDIAC PACING AND SENSING CONFIGURATIONS FOR USE WITH AN IMPLANTABLE MEDICAL DEVICE

FIELD OF THE INVENTION

The invention generally relates to implantable cardiac stimulation devices such as pacemakers, implantable cardioverter-defibrillators (ICDs) and cardiac resynchronization therapy (CRT) devices and, in particular, to techniques for optimizing and controlling multi-site left ventricular (MSLV) pacing and sensing functions for use with devices equipped with multi-pole LV leads.

BACKGROUND OF THE INVENTION

Some implantable cardiac stimulation devices are equipped with multi-pole LV leads, i.e. leads provided with a set of electrodes sufficient to permit multi-site LV (MSLV) pacing. For such devices, it is desirable to determine optimal MSLV interelectrode pacing delays for use in delivering MSLV pacing. The MSLV interelectrode pacing delays can, for example, specify time delays between delivery of electrical pacing pulses at different sites within the LV or along different pacing vectors. The MSLV pulses may be coordinated with the delivery of pulses to the RV via a bipolar RV lead so as to improve cardiac hemodynamics. In particular, MSLV pacing may be coordinated with RV pacing to provide CRT pacing, which seeks to normalize asynchronous cardiac electrical activation and resultant asynchronous contractions associated with congestive heart failure (CHF) by delivering synchronized pacing stimulus to both ventricles. The RV and MSLV stimulus are synchronized so as to improve overall cardiac function. This may have the additional beneficial effect of reducing the susceptibility to life-threatening tachyarrhythmias.

U.S. patent application Ser. No. 12/607,817, filed Oct. 28, 2009, of Ryu et al., entitled "Systems and Methods for Optimizing Multi-Site Left Ventricular Pacing based on Interelectrode Conduction Delays", which is fully incorporated by reference herein, describes systems and methods for determining preferred or optimal MSLV interelectrode pacing delays for use with MSLV pacing, particularly MSLV CRT. Other techniques described therein are directed to determining preferred or optimal combinations of LV electrodes or permutations of MSLV pacing vectors for use in delivering MSLV pacing using a multi-pole LV lead.

The present invention is directed, inter alia, to providing techniques for automatically and efficiently optimizing pacing and sensing configurations for use with MSLV-equipped cardiac rhythm management devices or other suitable implantable medical devices.

SUMMARY OF THE INVENTION

In accordance with a first exemplary embodiment of the invention, generally referred to herein as "QuickStim," a method is provided for controlling the delivering stimulation therapy for use with an implantable cardiac stimulation device equipped to delivery pacing or other stimulation therapy in accordance with a selectable set of stimulation control parameters, such as particular pulse vectors, pulse amplitudes or pulse widths. Briefly, a degree of hemodynamic benefit expected to be achieved using each of a plurality of sets of stimulation control parameters is assessed. A degree of device longevity expected to be achieved using each of the plurality of sets of stimulation control parameters is also assessed. A particular set of stimulation control parameters is then selected or determined based on the degree of hemodynamic benefit and the degree of longevity. Stimulation therapy is then controlled in accordance with the selected set of stimulation control parameters.

In one example, the clinician specifies a desired degree of bias or balance between device longevity and hemodynamic benefit (e.g. improved cardiac performance), and then the implantable device (or an external programmer system in communication with the device) operates to determine a particular pacing configuration for the patient that will achieve the desired degree of bias or balance. In this regard, an increase in hemodynamic benefit often requires the use of more stimulation pulses, particularly within MSLV systems, thus consuming more battery power and reducing the overall longevity of the device. Hence, an increase in hemodynamic benefit may come at the expense of device longevity, or vice versa. By assessing the degree of hemodynamic benefit and the degree of longevity expected with various pacing configurations, the device/system can identify particular pacing configurations that are sufficient to achieve the degree of bias specified by the clinician. In this manner, the clinician can easily program the implanted device to achieve a desired balance between hemodynamic benefit and/or device longevity.

In an illustrative implementation where the implantable device is equipped for MSLV pacing, the device/system operates to determine a preferred or optimal set of MSLV pacing control parameter configurations, with each configuration specified by: a particular set of MSLV pacing vectors; a number of MSLV pacing pulses to be delivered during each cardiac cycle using the pacing vectors; the pulse amplitudes of the MSLV pulses; the pulse widths of the MSLV pulses, and various MSLV pacing intervals (such as MSLV interelectrode pacing intervals.) For each of a set of candidate MSLV pacing configurations, the device/system assesses the hemodynamic benefit expected to be achieved within the patient using one or more pacing tests during which various parameters or "factors" representative of MSLV pacing efficacy are measured. Such MSLV pacing efficacy factors can include: paced QRS duration; cardiac output and/or cardiac output surrogates; contractility and/or contractility surrogates; mechanical synchrony; the degree of fractionation of the LV or RV intracardiac electrogram (IEGM); and the activation time to non-paced sites in the LV or RV, etc. That is, for each candidate MSLV configuration, the device delivers a set of test MSLV pulses and measures the resulting MSLV pacing efficacy factors to assess hemodynamic benefit. In some cases, pacing efficacy can be estimated without requiring a full set of pacing tests.

Likewise, for each of the set of candidate MSLV pacing configurations, the device/system assesses or estimates the device longevity expected to be achieved within the patient. This may be accomplished, e.g., by using predetermined mathematical models of current drain on the power supply of the particular model of the implanted device, along with measured lead impedance values of the leads of the device and any ongoing heart rate trends detected within the patient. For each candidate MSLV configuration, the device/system obtains and uses this information to estimate the expected power supply longevity within the patient. Then, based on the hemodynamic benefit and the expected device longevity, the device/system determines how well each candidate MSLV configuration matches the desired bias or balance value input by the clinician. This assessment can then be displayed by an external system to allow the clinician to select from among the best candidates. In some examples, the device itself may be configured to use the assessment information to automatically select the best candidate and to then reprogram its operation accordingly.

Within state-of-the-art MSLV systems, there might be quite a large number of "permutations" of MSLV pacing configurations (represented by different combinations of pacing vectors, pulse amplitudes, etc.) Accordingly, it is desirable to employ techniques for reducing the number or permutations that need to be tested to assess hemodynamic benefit or that need to be analyzed to estimate device longevity. In one example, an initial set of single-site pacing tests are performed using the individual electrodes of the MSLV lead to identify any sites that are unacceptable for various reasons, such as poor capture thresholds, long activation delays, pulse fusion, the triggering of unwanted phrenic nerve stimulation, etc. All permutations associated with any and all unacceptable LV sites are then excluded from further analysis. Bipolar configurations including the excluded unipolar electrode(s) can be tested once to determine if they are also unacceptable according to hemodynamic factors. Any dual- and triple-site configurations containing unacceptable bipolar single-site configurations can also be excluded from further testing.

Still further, to reduce the number of multi-pacing-site tests, the time interval from test pacing pulses to sensed activation at each non-paced electrode is measured. Any potential intraventricular timing intervals longer than the sensed interval are excluded from the range of intervals to be tested. Further, measured intraventricular delays below a threshold interval serve to exclude the choice of sequential pacing from the originally paced to short-interval sensed electrodes, as the result of a second pulse would be fusion with the propagating excitation after the first pulse, thereby wasting the energy of the second pulse.

Thereafter, only non-excluded sites are fully tested to assess hemodynamic benefit and to estimate device longevity. In one example, for a given MSLV vector configuration, the device iteratively adjusts pulse amplitudes through predetermined ranges of values to assess resulting hemodynamic benefits. Various timing intervals may be iterated as well. However, in a preferred embodiment, the optimal timing is estimated rather than iterated based on sensed interelectrode timings, such that the most delayed regions are stimulated earliest and the remaining pulses, when appropriate, are timed in order to achieve the maximal simultaneous electrical activation. This may be estimated using a variety of techniques, described below.

In some examples, pacing configurations are identified that achieve dual-site capture using a bipolar pacing vector. This may be desirable in cases in which a multisite configuration calls for two unipolar vectors with a short interelectrode delay, and where the two unipolar electrodes are constituents of an allowable bipolar vector. The bipolar vector, when paced at low amplitudes, results in single-site capture at the cathode, but when paced at higher amplitudes, can result in dual-site capture at both cathode and anode. Thus, "virtue" dual-site simultaneous capture can be achieved. Based on the impedance at each electrode and the individual capture thresholds of each unipolar and bipolar configuration, it may cost less in terms of battery drain to stimulate the bipolar configuration at higher output rather than using two lower output unipolar pacing pulses. Resultant activation and/or hemodynamics are preferably tested in the unipolar and bipolar configurations in order to ensure comparable outcomes.

Based on estimated or measured resultant activation and hemodynamics from each pacing configuration whose constituent vectors satisfy pacing efficacy factors, and also based on estimated battery drain for each configuration, the remaining non-excluded configurations (single and multisite) are weighed against how well the configurations satisfy the clinician-defined bias or balance between improved cardiac performance and battery longevity. The configurations that satisfy the balance are then preferably tested (not estimated at this point) with multiple fine-tuning iterations so as to incrementally shift the improvement in performance and energy savings, while modulating pacing voltage and pulse width and tweaking interelectrode timings slightly above and below the estimated values to yield optimized configurations.

Thereafter, each of the optimized configurations is ranked based on a score derived from how well the configurations match the clinician-defined balance or bias value. The output of the ranking procedure can be, e.g., an ordered list of configurations along with their overall scores (according to the balance) and, in some examples, also including individual scores for hemodynamics and longevity. In an example where the procedure is performed by the device itself outside of a medical office, clinic or hospital, the preferred (i.e. winning) configuration may be programmed by the device or stored therein for later retrieval. When run in-clinic using a device programmer, the clinician is prompted to select a particular configuration and, in one example, can move an input "slider-bar" to shift the aforementioned balance value and then see re-computed scores and rankings so as to identify a particular configuration that is suitable.

In some situations, it is possible that the clinician knows a priori that he or she wants to program, for example, two pacing pulses. Other up-front assumptions or constraints may also be made. In light of such constraints, some implementations are equipped to automatically limit the number of vectors to be tested to only those that meet those a priori conditions, and to then determine the resulting factors and estimated device longevity. In this case, the balance would be more strongly to a "custom" preference rather than to hemodynamic or device optimization.

In accordance with a second exemplary embodiment of the invention, generally referred to herein as "QuickSense," a method is provided for controlling the sensing of cardiac signals for use with an implantable cardiac stimulation device equipped to record electrical cardiac signals from a selectable set of sensing vectors using a plurality of sensing channels. Briefly, a sensing profile is input that is representative of preferred cardiac signal sensing features or sensing factors. An amount by which each set of sensing vectors matches the input sensing profile is assessed. A particular set of sensing vectors for use in cardiac sensing is then selected or determined based on the degree to which each set of sensing vectors matches the factors of the input sensing profile. Thereafter, cardiac signals are sensed using the selected set of sensing vectors.

In this regard, given the number of electrodes in a state-of-the-art MSLV lead system, many possible sensing vectors are available. However, despite the number of possible sense vectors, many devices (such as pacemakers, ICDs, CRT-D, etc.) are limited in the number of sensing channels that can be used simultaneously and/or to the number that can be recorded simultaneously. For example, in some devices, there are only four sensing channels and only two of those channels can be set to record simultaneously. The choice of which vectors are best for sensing/recording depends on electrode position with respect to patient cardiac anatomy and underlying tissues and on what sensed features are of most interest to the clinician. To that end, clinician-specified sensing profiles are exploited to determine which sensing configurations should be used for sensing and/or recording cardiac signals based on a set of clinician-specified sensing factors.

In one example, all available unipolar and bipolar sensing configurations are sequentially recorded over several cardiac cycles using the available sensing channels to determine values for the sensing factors for each vector. The sensing factors specified by the clinician can include: V-wave amplitude (wherein the V-wave represents a portion of the QRS-complex), timing values, paced depolarization intervals (PDIs) derived from QRS-complexes, and QRS morphology (in intrinsic rhythm and/or in paced rhythm); similar features for T-waves in intrinsic and paced rhythm; beat-to-beat consistency; respiration effects on the signal; signal noise; the presence, amplitude, and/or timing of far-field atrial signals or far-field ventricular signals; and/or electrode location with regard to known landmarks or myocardial substrates. Measured values for these sensing factors are temporarily stored for use with computing a sensing profile score for each sensing vector.

Based on the sensing factor values and the sensing profile chosen, it is possible that only one or two sensing vectors will be sufficient and, if so, the sensing channels of the device are programmed to sense signals using these vectors. In other cases, three or more sense vectors might be necessary. If so, and if the device can only record two channels at a time, then various "virtual" sensing channels can be created. For example, if all of the desired sense vectors are unipolar, then separable combinations of the unipolar vectors can be used to create two bipolar vectors for sensing. In one particular example, if the optimal sense vectors are Tip-Case, R1-Case, and R2-Case, then in order to record all three on no more than two sense channels the system might recommend recording Tip-R1 and R2-R1 as bipolar sense vectors; then the R1 "virtual unipolar" signal can be separated as the common-mode signal, and the Tip "virtual unipolar" and R2 "virtual unipolar" signals are separated by common-mode rejection or subtraction of the R1 virtual unipolar signal.

If some of the desired sense vectors are bipolar or there are too many desired sense vectors to create two separable bipolar channels, then a multiplexed sensing scheme can be used in which each of the two available sense channels alternate among the various desired sense vectors on a beat-by-beat basis or on a sample-by-sample basis. For example, if Tip-R1, R2-Case, and R3-Coil are needed based on the sensing factors and sensing profile, then one sense channel may alternate each beat or every 2nd or 3rd beat between R2-Case and R3-Coil, or each sample may alternate as such. The beats or samples are associated using a predetermined (i.e. known) scheme with the various sensing vectors, such that the microprocessor software or electronics of the device can later separate the signals. In some examples, "gating" or "anisotropic oversampling" is employed, which are described below.

Based on the sensing factors and the sensing profile, the device/system then recommends one or more sense configurations based on various rankings. In the case of in-clinic follow-up, the recommended sensing configurations are displayed on the programmer screen to allow the user to select or customize a particular configuration. In the case of device-based auto-sense-configuration, the recommended configuration can be stored for notification at the next follow-up (or via remote transmission and/or permanently programmed.) In some cases, it might instead be appropriate for the device to automatically switch to the recommended sensing configuration, particularly if a currently programmed sensing configuration is found to be inadequate.

In a preferred implementation, the recommendations provided by the QuickSense system specify the particular sense vector(s) to configure on each of the available sensing channels, the particular sensitivity levels and blanking/refractory periods to be set, whether one or more channels should be multiplexed or gated, and whether multiplexing should include anisotropic oversampling. A "Details" screen may be provided as part of the user interface, which provides information to the user pertaining to what the sense channel recordings will look like (based on test sense data) and what confidence/risks are involved when using the recommended vectors rather than other vectors in relation to the sensing profile.

Depending upon the particular patient, the physician or clinician might have in mind the most-likely risks of a device for the patient. For example, some ischemic patients might be at higher risk for VT/VF episodes, while dilated cardiomyopathy (DCM) patients might be at greater risk for loss of BiV capture due to intrinsic fusion resulting in deteriorating hemodynamics. As such, the "optimal" sensing configurations for these patients can differ. The aforementioned sensing profiles offer the clinician a pre-set scheme for weighing the many factors that go into optimizing the sensing configuration. Thus, various factors can be collected/measured during a sense test for each sense vector. The choice of sensing profile then determines how to weigh the factors to yield a final QuickSense score. In some examples, there will be a separate profiles specified for: maximizing arrhythmia detection; ensuring maximum BiV pacing; optimizing VV and intra-V timing intervals and/or activity-response slope; allowing for diagnostics such as evoked response diagnostics, etc. Thus, based on the requirements for each individual patient, the weighting factors of QuickSense are adjusted when recommending an "optimal" sense configuration.

Although summarized primarily with respect to implementations having a multi-pole LV lead, aspects of the invention are also generally applicable to systems with other multi-pole leads, such as multi-pole RV leads or multi-pole atrial leads, or to devices that do not employ multi-pole leads.

BRIEF DESCRIPTION OF THE DRAWINGS

Features and advantages of the described implementations can be more readily understood by reference to the following description taken in conjunction with the accompanying drawings.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of Implantable System

Figure 1:
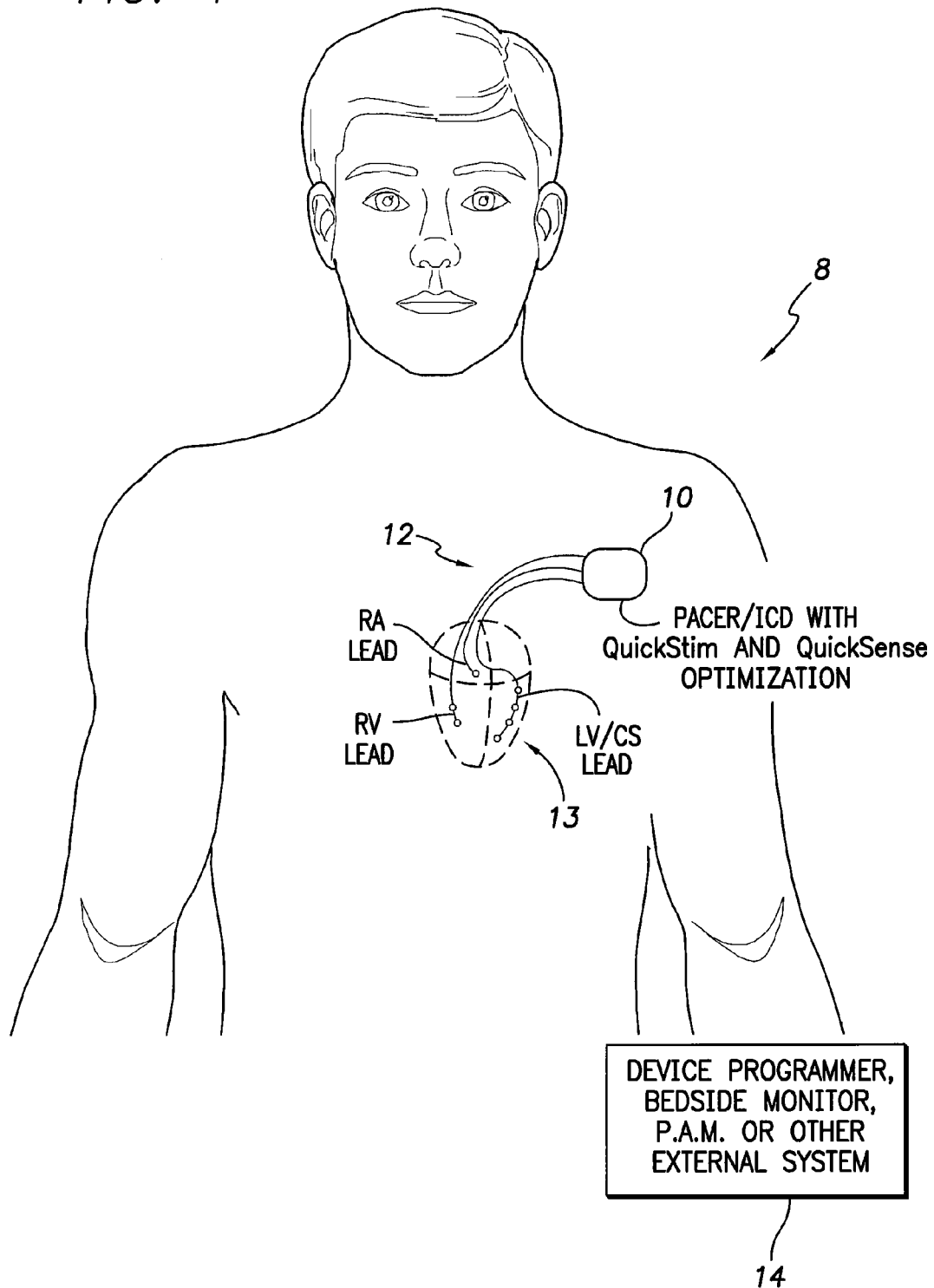
FIG. 1 illustrates pertinent components of an implantable medical system having a pacemaker, ICD or CRT-D device equipped to implement QuickStim and QuickSense techniques.

FIG. 1 illustrates an implantable medical system 8 capable of optimizing pacing and sending configurations. The medical system 8 includes a pacer/ICD 10 or other cardiac stimulation device (such as a CRT-D or CRT-P) equipped with one or more cardiac sensing/pacing leads 12 implanted on or within the heart of the patient, including a multi-pole LV lead implanted via the coronary sinus (CS). To illustrate the multi-pole configuration of the LV lead, a set of electrodes 13 is shown distributed along the LV lead. The RV and RA leads are each shown with a single electrode, though each of those leads may include additional electrodes as well, such as bipolar tip/ring electrode pairs, shocking coils, etc. Still further, the LV lead can also include one or more left atrial (LA) electrodes mounted on or in the LA via the CS, as well as additional shocking coils. See FIG. 12 for a more complete and accurate illustration of various exemplary leads.

Broadly, two main optimization functions are described herein. The first, QuickStim, seeks to optimize or adjust pacing stimulation configurations employed by the device to, e.g., achieve a clinician-specified degree of balance or bias between hemodynamic benefit and device longevity. The second, QuickSense, seeks to optimize or adjust sensing configurations employed by the device to, e.g., satisfy a clinician-specified sensing profile. In some implementations, the pacer/ICD itself performs these optimization functions based on specifications originally input by a clinician using an external system and then transmitted via telemetry to the pacer/ICD. In other implementations, an external device programmer 14 (or other external or remote system) performs the functions based on cardiac signals and other parameters sensed within the patient by the pacer/ICD and then transmitted to the external system for analysis. That is, the external programmer determines the optimal or preferred pacing/sensing configurations for the patient and then sends suitable programming commands to the pacer/ICD for programming the device to employ those pacing/sensing configurations. Note that other external devices might instead be used to perform the QuickStim and QuickSense techniques, such as bedside diagnostic monitors, personal advisory modules (PAMs) or the like. In some embodiments, the external device is directly networked with a centralized computing system, such as the HouseCall™ system or the Merlin@home/Merlin.Net systems of St. Jude Medical for remote analysis.

In the following illustrative examples, unless otherwise noted it is assumed that the optimization is performed under the control of an external programmer in telemetric communication with the pacer/ICD while under clinician supervision. Depending upon the particular features being described, some steps/functions will be performed by the pacer/ICD, others by the external programmer. Collectively, the pacer/ICD and external programmer device are generally referred to as the system.

"QuickStim" Pacing Configuration Optimization

Figure 2:
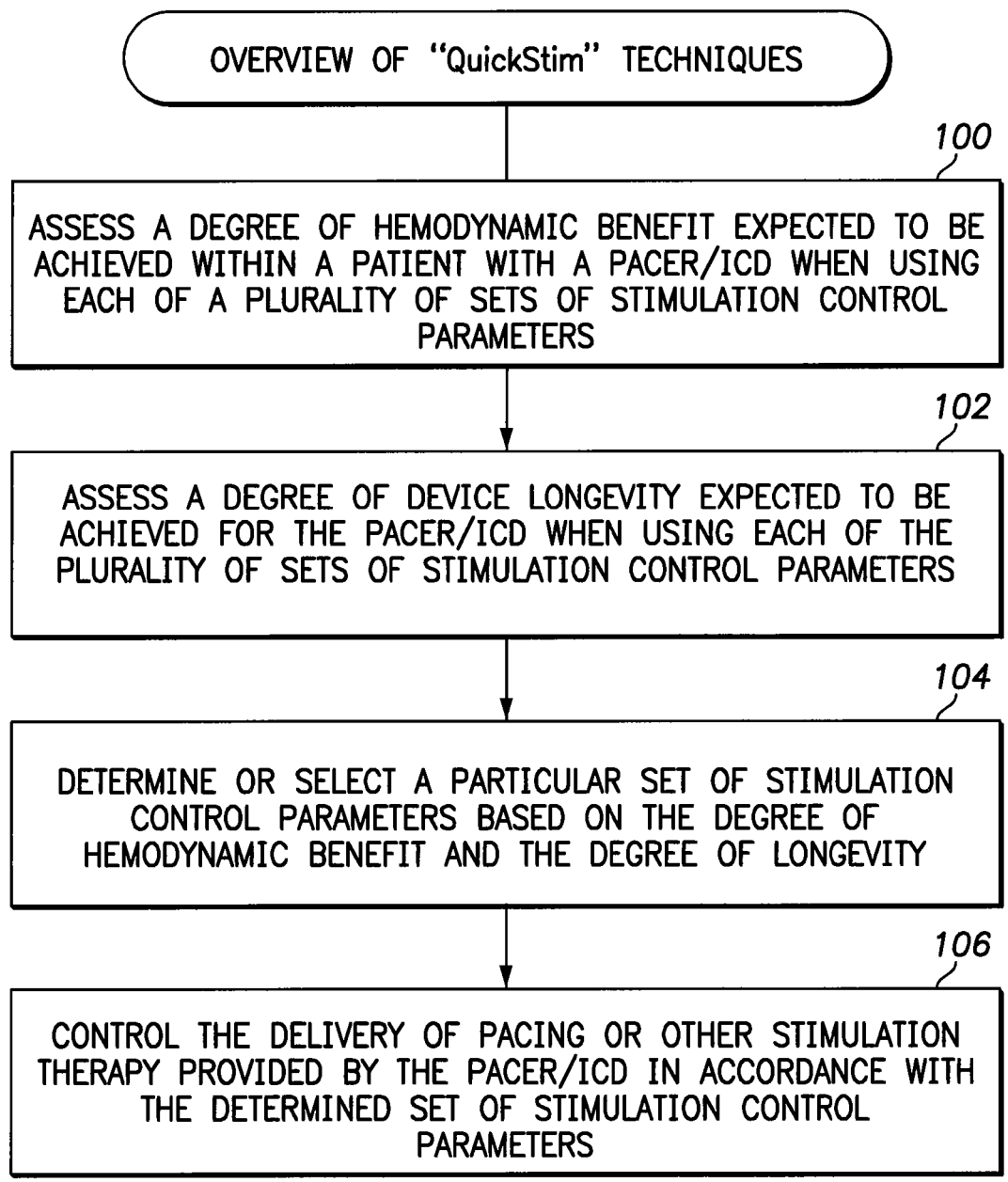
FIG. 2 summarizes a general QuickStim technique for setting cardiac stimulation control parameters based on hemodynamic benefit and device longevity, which may be performed by the system of FIG. 1.

FIG. 2 broadly summarizes a general technique that may be exploited by the system of FIG. 1 (or other suitably-equipped medical systems) for setting cardiac stimulation control parameters based on hemodynamic benefit and device longevity. Beginning at step 100, the system assesses the degree of hemodynamic benefit expected to be achieved using the pacer/ICD within a particular patient when using each of a plurality of sets of stimulation control parameters. Each unique set of stimulation control parameters may also be referred to as a "pacing configuration." The assessment of the hemodynamic benefit may be based on a variety of cardiac stimulation parameters or "pacing factors" detected within the patient by the pacer/ICD and then transmitted to the device programmer. These factors are generally representative of pacing efficacy and can include, e.g.: activation time to non-paced sites; QRS durations; fractionation values; cardiac output and/or cardiac output surrogates; contractility and/or contractility surrogates; and mechanical synchrony.

Briefly, the activation time delay represents the time from delivery of V-pulses to a resulting paced depolarization event and can be measured at any nonpaced site in the LV or RV. A vector that yields the quickest activation time is generally preferred. In some examples, only RV activation times are assessed. In other examples, only LV activation times are assessed. QRS duration represents the "width" or time duration of a paced QRS detected at a location other than the pacing site. LV or RV QRS duration (or both) can be tracked. The vector that yields the shortest QRS durations is preferred. Insofar as fractionation is concerned, LV and/or RV IEGM signals (sensed at various sites) can be examined to assess the degree of fractionation of the cardiac signal. The degree of fractionation relates to the degree of continuity of the paced QRS (or an evoked response) and may be quantified by template matching, feature characterization, or frequency information such as fast Fourier transform (FFT) spectra. See, for example, U.S. Pat. No. 7,440,804 to Min, et al. Fractionation can also be assessed based on cardiogenic impedance signals. See, for example, U.S. Patent Application 2008/0262361 of Guffinger et al. When used in conjunction with an external monitor, any of these parameters might instead be detected by the external monitor and then transmitted to the implanted device for processing therein (and/or the parameters could be transferred to the device programmer for use therein in controlling the optimization procedure.)

Techniques for detecting contractility are discussed in, e.g., U.S. Pat. No. 6,788,970 to Park, et al., entitled "System and Method for Treating Vasovagal Syncope using Cardiac Pacing." Techniques for detecting cardiac output within a patient using an implantable medical device are described, e.g., in U.S. patent application Ser. No. 11/267,665, filed Nov. 4, 2005, of Kil et al., entitled "System and Method for Measuring Cardiac Output via Thermal Dilution using an Implantable Medical Device with Thermistor Implanted in Right Ventricle."

At step 102, the system assesses the degree of device longevity expected to be achieved by the pacer/ICD when using each of the plurality of sets of stimulation control parameters. Device longevity is assessed based, e.g., on predetermined mathematical models of current drain on the power supply of the particular model of the pacer/ICD along with other relevant parameters, discussed below. At step 104, the system then selects or determines a particular set of stimulation control parameters (i.e. a particular pacing configuration) based on the degree of hemodynamic benefit and the degree of longevity for use in controlling the delivery of pacing stimulation in the patient. In an example to be described in greater detail with reference to FIG. 2, the system identifies the particular pacing configuration that most closely achieves a clinician-specified degree of bias or balance between hemodynamic benefit and device longevity. At step 106, the system then controls the delivery of pacing or other cardiac stimulation therapy in accordance with the determined or selected set of stimulation control parameters, i.e. in accordance with the selected pacing configuration. In this manner, pacing configurations can be set or optimized based on parameters representative of hemodynamic benefit and device longevity to achieve desired results within the patient.

Figure 3:
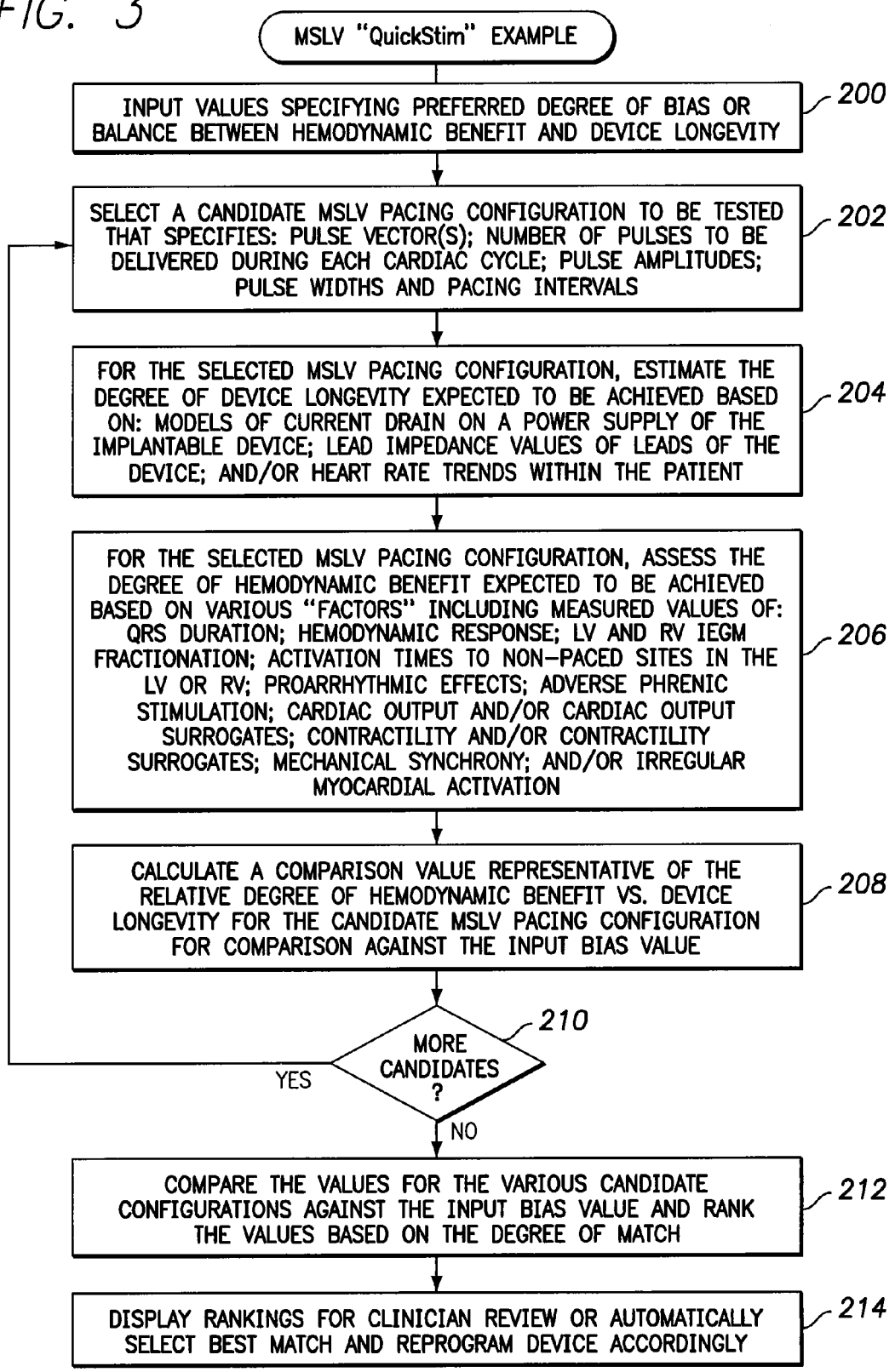
FIG. 3 illustrates an MSLV QuickStim example based on the general QuickStim technique of FIG. 2, wherein a preferred degree of bias or balance between hemodynamic benefit and device longevity is exploited.

FIG. 3 provides further details pertaining to an MSLV implementation wherein the QuickStim techniques operate to identify an MSLV pacing configuration that most closely matches a degree of bias between hemodynamic benefit and device longevity input by a clinician. Beginning at step 200, the system inputs values specifying a preferred degree of bias or balance between hemodynamic benefit and device longevity from a clinician via a device programmer or other external system. The degree of bias might be numerically specified, e.g., on a scale of 1-100 wherein 1 indicates that the bias should be strongly in favor of device longevity and 100 indicates that the bias should be strongly in favor of hemodynamic benefit.

At step 202, the system selects a candidate MSLV pacing configuration to be tested from among a set of possible MSLV pacing configurations/permutations wherein the pacing configuration specifies: the particular MSLV pulse vector(s) to be used; the number of MSLV pulses to be delivered during each cardiac cycle; pulse amplitudes; pulse widths and pacing intervals such as interelectrode pacing delays. At step 204, for the selected MSLV pacing configuration, the system estimates the degree of device longevity expected to be achieved based on: predetermined models of current drain on a power supply of the implantable device; lead impedance values of leads of the device; and/or heart rate trends within the patient.

At step 206, for the selected MSLV pacing configuration, the system assesses the degree of hemodynamic benefit (or pacing efficacy) expected to be achieved based on various pacing factors including measured values of:

activation time to non-paced sites in the LV or RV
QRS duration (at nonpaced sites in the LV or RV)
degree of LV or RV IEGM fractionation
hemodynamic response such as cardiac output and/or cardiac output surrogates, stroke volume, contractility and/or contractility surrogates; or mechanical synchrony (as detected by the implanted device or by an external monitor.)

Other pacing factors that might also be assessed include: parameters indicative of proarrhythmic effects, parameters indicative of adverse phrenic stimulation, and/or parameters representative of irregular myocardial activation (at either non-paced LV sites or non-paced RV sites).

As to hemodynamic response, depending upon the capabilities of the device, some measure of hemodynamic response can be assessed by the device itself, such as cardiac output, stroke volume, left atrial pressure (LAP) or some suitable measure of cardiogenic impedance. See, for example, U.S. Pat. No. 7,139,609 to Min, et al. In some examples, an external monitor is used to assess hemodynamic response and the parameters representative of that response are transmitted to the implanted device for processing therein (and/or the parameters are transferred to an external programmer for use therein in controlling the optimization procedure.)

Note that if several different parameters representative of hemodynamic benefit or pacing efficacy are measured by the device at step 206, these parameters can be combined to produce a single "metric" value for assessing the overall degree of pacing efficacy of pacing configurations. Note also that steps 204 and 206 need not be performed in the order shown in FIG. 3. Longevity can instead be assessed first or, in some embodiments, longevity and hemodynamic benefit can be assessed concurrently.

At step 208, the system calculates a comparison value or "score" representative of the relative degree of hemodynamic benefit vs. device longevity for the candidate MSLV pacing configuration for comparison against the input bias value. Assuming there are more pacing configurations to be tested, as determined at step 210, the system returns to step 202 to select a different pacing configuration and the assessment procedure is repeated. (Various "shortcut" techniques are discussed below for reducing the total number of pacing tests.)

Once the last of the candidates has been tested, processing proceeds to step 212 wherein the system compares the values or scores for the various candidate configurations against the input bias value and ranks the values based on the degree of match. At step 214, the system displays the rankings for clinician review or, in some implementations, the system automatically selects a best match and reprograms the pacer/ICD accordingly. Clinician review is preferred. However, in some circumstances, such as if there is a sudden problem with a current MSLV pacing configuration (due, e.g., to a failure of a given electrode or due to lead dislodgement), it might be appropriate for the pacer/ICD to automatically perform the overall QuickStim assessment and then switch to a new pacing configuration, or to automatically revert to the "next-best" pacing configuration from the prior QuickStim assessment, to ensure proper ongoing pacing therapy, pending subsequent clinician review.

Figure 4:
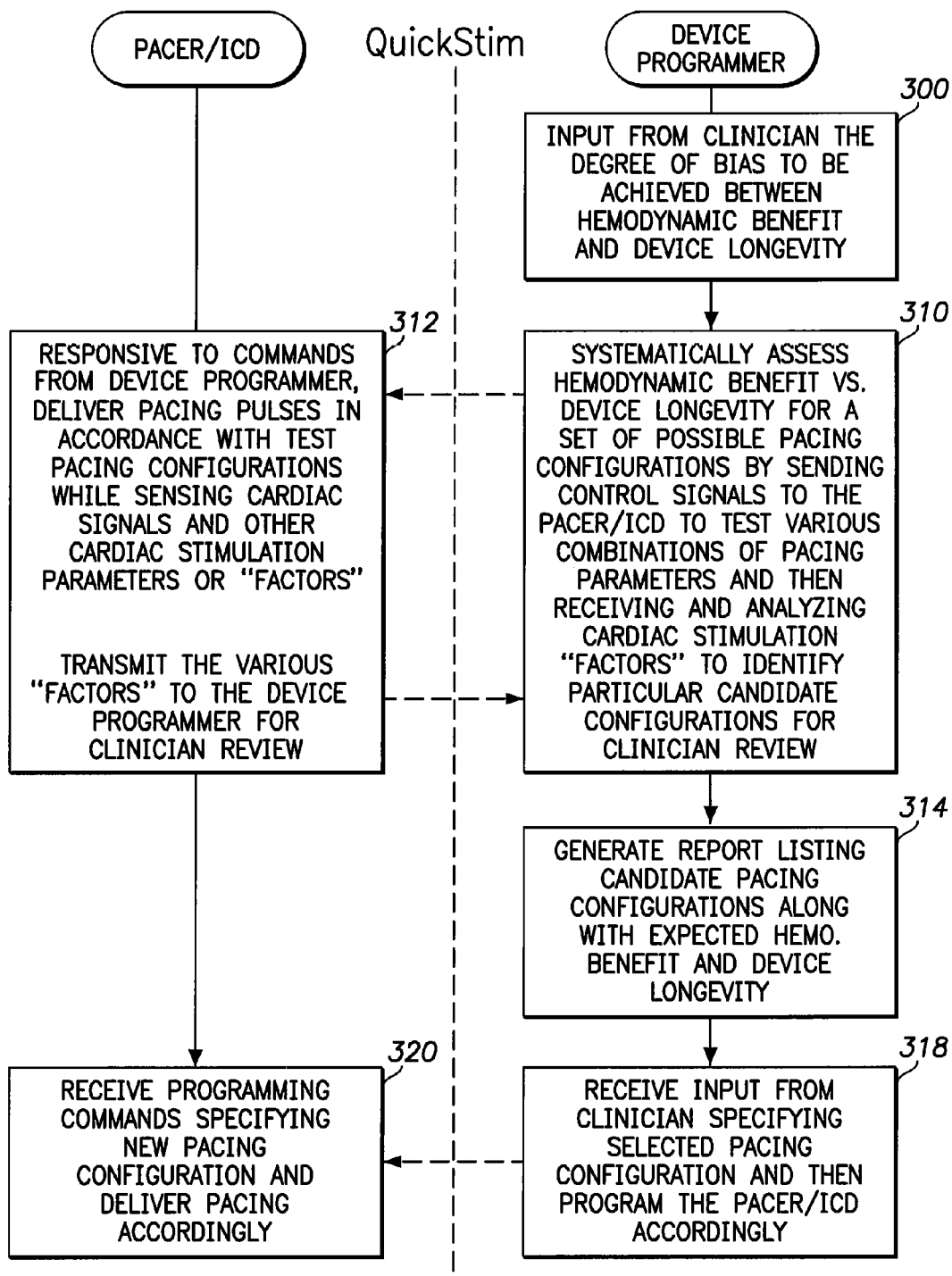
FIG. 4 is a flowchart illustrating an exemplary implementation of the MSLV QuickStim technique of FIG. 4, wherein the implanted device operates in conjunction with an external programmer system.
Figure 5:
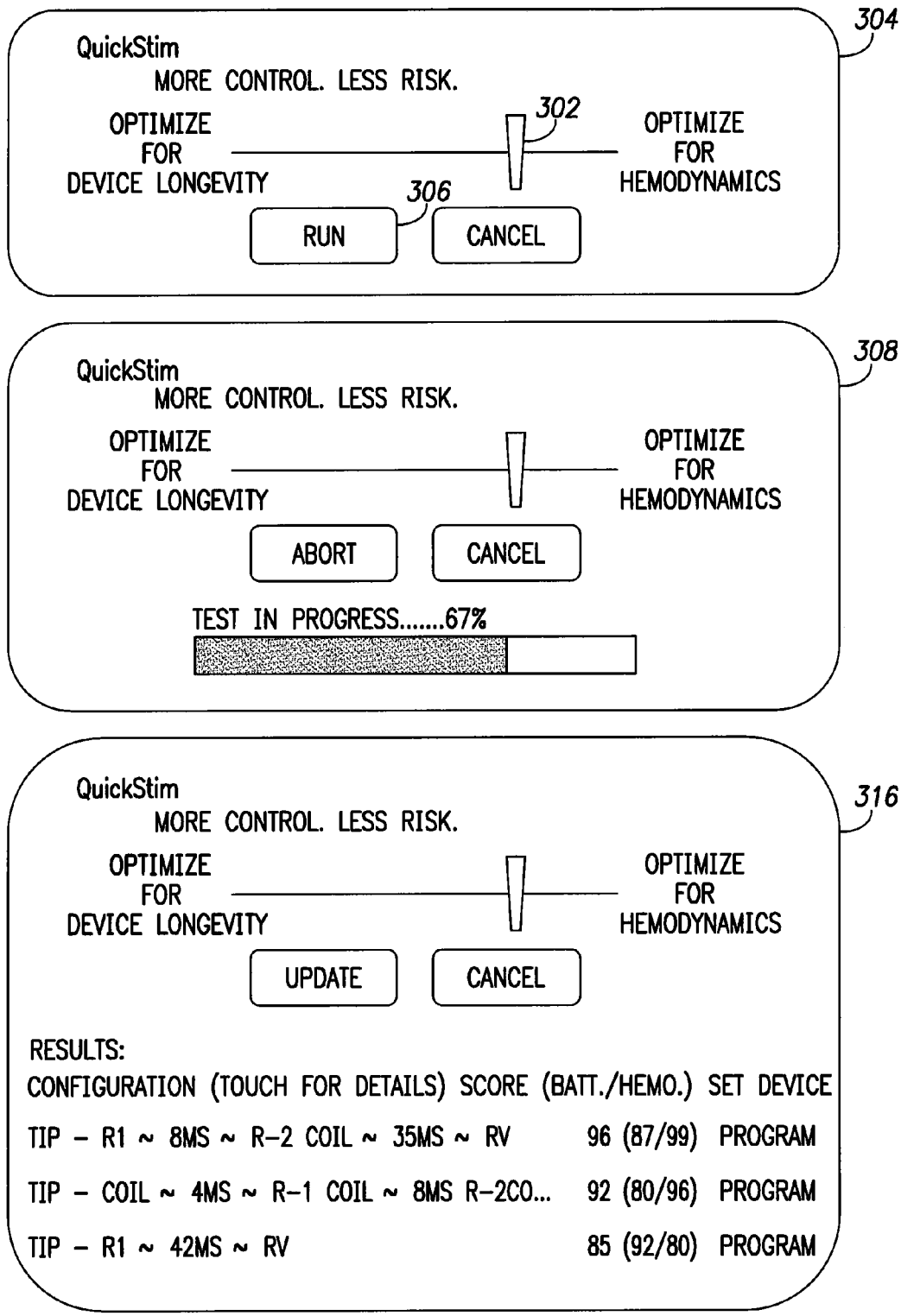
FIG. 5 illustrates exemplary input/display screens that may be generated by the external system of FIG. 4.

Turning now to FIGS. 4 and 5, QuickStim techniques will be described with reference to an in-clinic example performed under clinician supervision. Operations performed by the pacer/ICD are shown on the left; operations performed by the device programmer are shown on the right. At step 300, the external device programmer inputs from the clinician the degree of bias or balance to be achieved between hemodynamic benefit and device longevity. This value may conveniently input using a slide bar 302, as shown in FIG. 5, which is part of a graphical input display 304 generated and displayed by the device programmer. The clinician, using a mouse controller, touch screen, or other suitable input device, slides or repositions the slide bar to a desired point between the opposing ends points of "optimize for device longevity" and "optimize for hemodynamics". The more closely the bar is set to "optimize for hemodynamics," the more the system will seek to find a pacing configuration that maximizes hemodynamics (perhaps at the expense of reduced device longevity.) The closer the bar is set to "optimize for device longevity," the more the system will seek to find a pacing configuration that maximizes device longevity (with less concern for hemodynamics.)

As noted above, an increase in hemodynamic benefit often requires the use of more stimulation pulses, particularly within MSLV systems, thus consuming more battery power and reducing the overall longevity of the device. Hence, an increase in hemodynamic benefit may come at the expense of device longevity, or vice versa. By assessing the degree of hemodynamic benefit and the degree of longevity expected with various pacing configurations, the system can identify particular pacing configurations that are sufficient to achieve the degree of bias or balance specified by the clinician. In this manner, the clinician can easily program the implanted device to achieve a desired degree of hemodynamic benefit and/or device longevity.

It should be understood that—even when set to optimize for device longevity—the pacer/ICD will still pace the heart to provide hemodynamic benefit to the patient. It is the degree of hemodynamic benefit (e.g. "aggressiveness" of the pacing) that is adjusted. For example, in a patient without significant heart failure, it might be inappropriate to provide aggressive MSLV pacing if it means the power supply of the device will be quickly depleted, requiring that the device be explanted and replaced (a procedure that has some risks.) Rather, in such a patient, it might instead be desirable to provide for less aggressive MSLV pacing so as to allow for longer device longevity while still achieving an acceptable level of hemodynamic benefit. This decision is preferably made by the physician or other clinician based on an overall evaluation of the needs of the patient. That is, the QuickStim system is not intended to replace the judgment of the clinician, but to more conveniently allow the clinician to identify a pacing configuration that will best serve the needs of the patient. Preferably, limits are provide to ensure the system does not set the pacer/ICD to inappropriate settings, such as a setting where maximum longevity is achieved simply by disabling all pacing.

Continuing with FIG. 5, once the clinician has set the slide bar, he or she initiates an automatic optimization procedure by "clicking" on the Run button 306. The device programmer then initiates a series of pacing tests intended to identify one or more pacing configurations that satisfy the bias criteria entered by the clinician. During the test, an indication is provided on the display screen as to the completion status of the test. See, e.g., exemplary display screen 308. This indication may be determined based on the total number of pacing configurations to be tested as compared to the number of tests already completed.

Returning to FIG. 4, the tests are performed beginning at step 310 wherein the device programmer systematically assesses hemodynamic benefit vs. device longevity for a predetermined set of possible pacing configurations and/or permutations by sending control signals to the pacer/ICD to test various combinations of pacing parameters and then receiving and analyzing the aforementioned cardiac stimulation "factors" to identify particular candidate pacing configurations for clinician review. To this end, a series of pacing tests is performed where the programmer sends control signals to the pacer/ICD to program the device to temporarily deliver pacing to the patient using a given pacing configuration. These tests are performed at step 312 wherein, responsive to commands from the programmer, the pacer/ICD delivers pacing pulses in accordance with test pacing configurations while sensing cardiac signals and other cardiac stimulation parameters or factors such as activation times, QRS durations, fractionation values, hemodynamic response values, etc. Upon completing a test with a given pacing configuration, the pacer/ICD transmits the measured factors to the device programmer for storage therein and subsequent clinician review. (In the case of external monitors, particularly for hemodynamics, these values are retrieved by the programmer and associated with the pacing configuration.) Still further, while the pacer/ICD is performing a given pacing test to measure hemodynamic benefit, the device programmer estimates device longevity for the pacing configuration being tested by using, for example, the aforementioned mathematical models of current drain along with measured lead impedance values received from the pacer/ICD and information pertaining to any heart rate trends and pacing percentage trends previously detected within the patient by the pacer/ICD and sent to the programmer.

The procedure of steps 310 and 312 continues until all pacing configurations and/or permutations of configurations to be tested have been tested and the results compiled. The tests can be cancelled by the clinician at any time by clicking on the Cancel button shown in FIG. 5. Note that various techniques for reducing the total number of tests to be performed will be described below. For each test, scores are calculated by the device programmer that indicate: the degree of hemodynamic benefit (for example on a scale of 1-100); the degree of battery longevity (also on a scale of 1-100); and a composite score (also on a scale of 1-100) indicative of the extent to which the given pacing configuration meets the bias or balance value input by the clinician.

At step 314, the device programmer then generates a report listing candidate pacing configurations that generally satisfy the criteria initially input by the clinician, along with a display of expected hemodynamic benefit and device longevity scores. See, e.g., exemplary display 316 of FIG. 5 wherein various pacing configurations are listed, as identified by a listing of specific pacing vectors and interelectrode pacing delay times therebetween. For the particular example of FIG. 5, a first candidate pacing configuration employed a first pulse delivered between LV Tip and LV R1, followed 8 ms later by a second pulse delivered between LV R2 and the RV coil electrode, followed 35 ms later by a unipolar pulse delivered using the RV tip electrode. The display also provides the aforementioned scores. In this case, the overall score is 96 indicating that the configuration comes close to achieving the particular degree of balance specified by the clinician. A second candidate configuration has a somewhat lower overall score. A third candidate has a still lower overall score, but with better battery longevity. By clicking or touching the display screen, the clinician can call up additional details regarding these configurations, including the recorded results of the pacing tests (including, e.g., lists of the particular factors measured during the test, as well as displays of resulting IEGMs, etc.) The clinician can then select a preferred pacing configuration from among the list of candidates.

At step 318 of FIG. 4, the device programmer receives input from clinician specifying the selected pacing configuration and then programs the pacer/ICD accordingly by transmitting suitable control signals. In the display example of FIG. 5, once a particular configuration has been selected, the clinician simply clicks the Update button to update the programming of the pacer/ICD. At step 320, the pacer/ICD receives the programming commands specifying the new pacing configuration, reprograms its components accordingly and then begins delivering pacing.

Figures 1, 6:
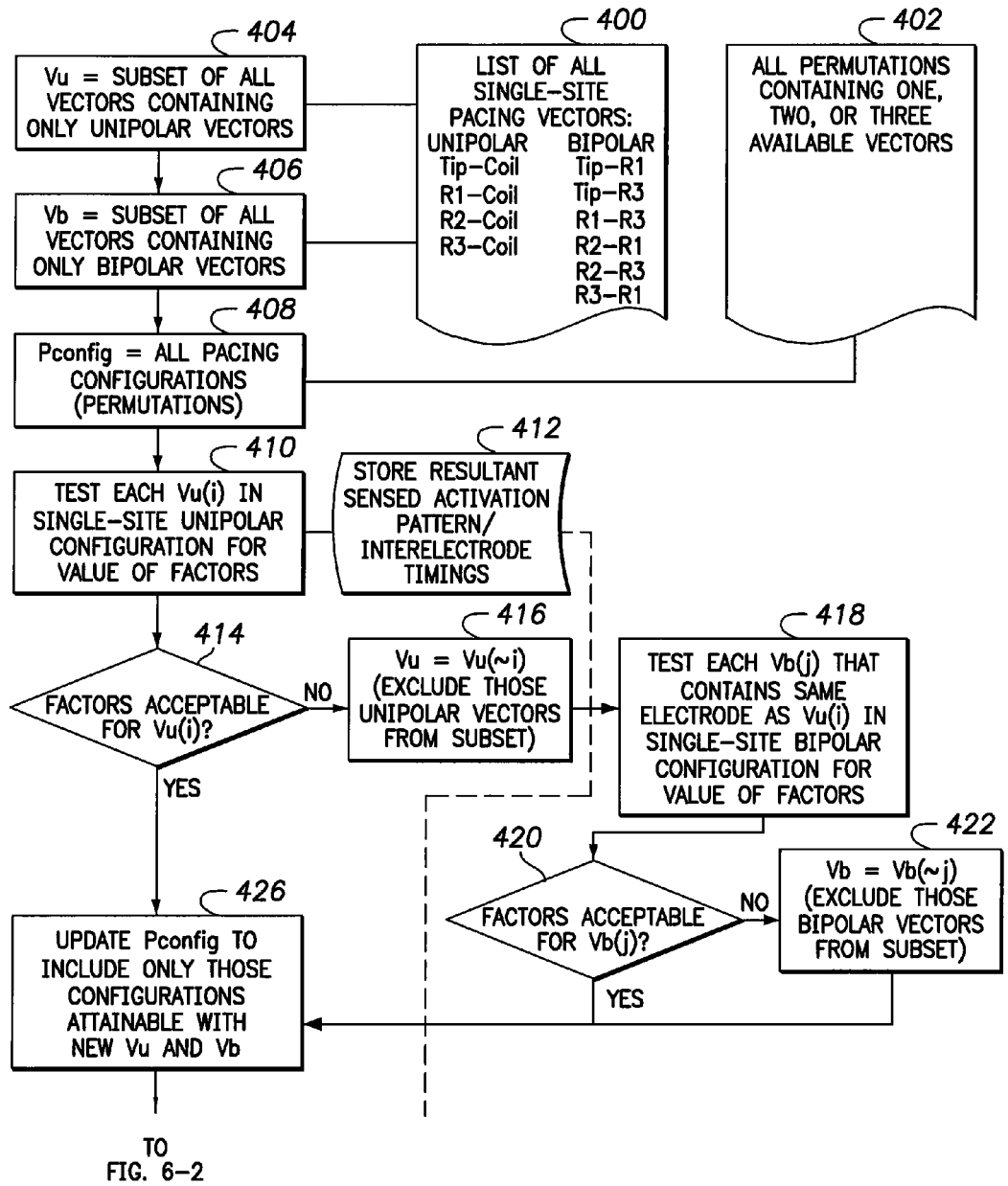
FIG. 6 illustrates a more detailed MSLV QuickStim example, also in accordance with the general technique of FIG. 2, which particularly illustrates various pacing optimization "short cuts"
Figures 2, 6:
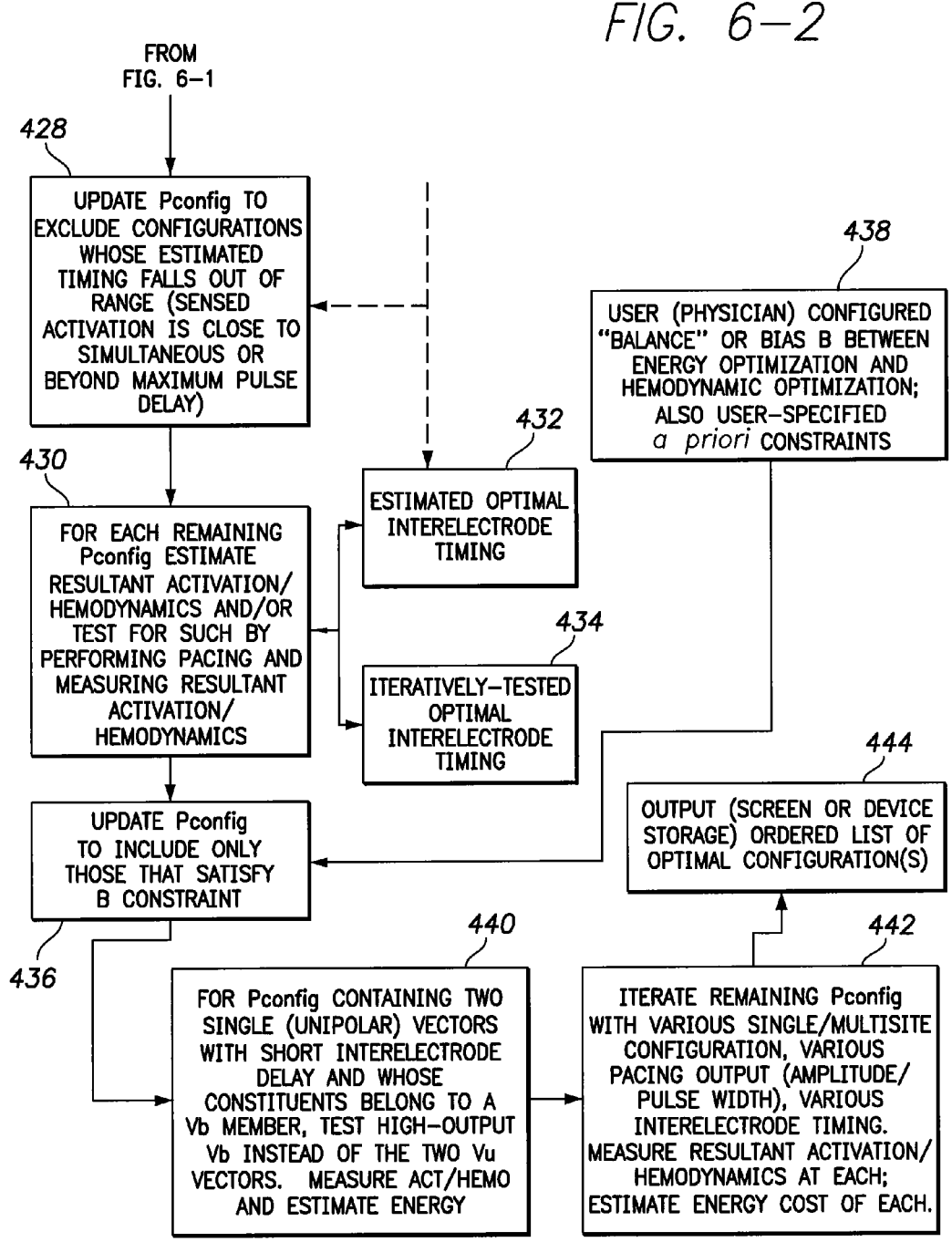

Turning now to FIG. 6, still further details are provided pertaining to an exemplary MSLV implementation, particularly one employing shortcut techniques for reducing the total number of pacing tests. Beginning at step 400, a list of all single-site unipolar and bipolar pacing vectors for the implanted pacer/ICD is retrieved from memory by the external programmer. In a particular example where the MSLV LV lead is a quadrapole (or "quadpole" or "quardipole") lead, the various programmable pacing vectors are as shown in Table 1. (In other examples, the device can or housing is used as the "return" electrode for unipolar vectors.)

TABLE I

| Unipolar | Bipolar |
| --- | --- |
| Tip-Coil | Tip-R1 |
| R1-Coil | Tip-R3 |
| R2-Coil | R1-R3 |
| R3-Coil | R2-R1 |
|  | R2-R3 |
|  | R3-R1 |

At step 402, the system identifies all of the permutations of these pacing vectors that contain one, two or three available vectors. For example, one permutation might be a three vector permutation where a first MSLV pulse is delivered bipolar Tip-R1, a second MSLV pulse is delivered bipolar R1-R3, and a third pulse is delivered unipolar Tip-coil. At step 404, the system generates an array Vu that represents the subset of all vectors containing only unipolar vectors. At step 406, the system generates a second array Vb that represents the subset of all vectors containing bipolar vectors. At step 408, the system generates an array Pconfig that represents all pacing configurations, i.e. all permutations retrieved at step 402.

At step 410, the system tests each Vu(i) in single-site unipolar configuration to determine values of each of the various factors listed above. At step 410, numerical values representative of these factors are obtained and stored. In particular, single-site testing can employ DDD or VDD LV pacing with short AV/PV delay or VVI LV pacing at base rate slightly above intrinsic rate (in order to ensure pure ventricular capture without fusion.) Also, at step 412, the system stores resulting sensed activation patterns and interelectrode timings for subsequent use. At step 414, the system evaluates the factors for Vu(i) to determine if the factors are acceptable. Depending upon the particular parameter, this can involve comparing the factor against one or more threshold values representative of acceptable values, which may be preprogrammed or specified by the clinician. Assuming that at least some of the factors are unacceptable for a given unipolar vector (i), then at step 416, the system excludes that unipolar vector from further consideration. This can greatly reduce the total number of test that need to be performed and hence represents one of the aforementioned shortcuts.

At step 418, the system then tests each Vb(j) that contains the same electrode as Vu(i) in single-site bipolar configuration to determine values for the aforementioned pacing factors. At step 420, the system evaluates the factors for Vb(j) to determine if the factors are acceptable. Assuming that at least some of the factors are unacceptable for a given bipolar vector (j), then at step 422, the system excludes that bipolar vector from further consideration. This likewise can reduce the total number of tests that need to be performed and hence represents another one of the aforementioned shortcuts.

Processing then proceeds to step 426 where the system updates Pconfig to include only those configurations attainable with new Vu and Vb (i.e. while excluding any configuration incorporating an excluded vector.) At step 428, the system then updates Pconfig to exclude pacing configurations whose estimated timing falls out of predetermined acceptable range (i.e. where sensed activation is close to simultaneous or beyond a maximum permissible pulse delay.) This step can use the activation and timing information previously stored at step 412.

At step 430, for each remaining Pconfig, the system estimates resultant activation/hemodynamics and/or tests for such by performing pacing while measuring resultant activation/hemodynamics. Estimates can be made, for example, by extrapolating or interpolating from known values for activation/hemodynamics for the particular patient or from patient populations. Estimated values for optimal interelectrode timing can be stored and/or retrieved at step 432. Iteratively-tested values for optimal interelectrode timing can be stored and/or retrieved at step 434.

Estimates can be based, at least in part, on information representative of global activation within the heart of the patient. For example, by using the sensing vector of RV coil to case (in a CRT-D system) or RA ring+RV ring to case (in a CRT-D or a CRT-P system) the sense amplifier of the device "sees" a broad unipolar-like signal that represents global activation. Other methods to see global activation include multiplexing the sense amplifier channel(s) to switch among various unipolar and bipolar vectors within a single cardiac cycle, or across several cycles, in order to get a more complete picture of LV global activation than achievable with a single sensing vector alone. Additionally, the resultant activation from each single site stimulation test at the earlier part of the algorithm can be stored, and an estimated resultant activation from the various permutations of pacing vectors can be computed as the superposition of each constituent measured activation, thereby reducing the number of tests.

Thereafter, at step 436, the system updates Pconfig to include only those permutations that satisfy any clinician or physician constraints B input at step 438, such as the aforementioned bias or balance between energy optimization (i.e. device longevity) and hemodynamic optimization (i.e. hemodynamic benefit.) In some situations, it is possible that the clinician knows a priori that he or she wants to program, for example, two pacing pulses and any such constraints or assumptions are input at step 438. Other up-front assumptions or constraints may also be entered at step 438. In light of such constraints, the system, at step 436, automatically limits the number of vectors to be tested to only those that meet the a priori conditions and to then determine the resulting factors and estimated device longevity (or other parameters such as avoidance of phrenic nerve stimulation.) In this case, the resulting balance would be more strongly to a "custom" preference rather than to hemodynamic performance or device optimization.

At step 440, for any Pconfig entries containing two single (unipolar) vectors with short interelectrode delay and whose constituents belong to a Vb member, the system tests high-output Vb instead of the two Vu vectors and measures activation/hemodynamics and estimates energy usage. That is, pacing configurations are identified that achieve dual-site capture using a bipolar pacing vector. This may be particularly desirable in cases where a multisite configuration calls for two unipolar vectors with a short interelectrode delay, and where the two unipolar electrodes are constituents of an allowable bipolar vector. The bipolar vector, when paced at low amplitudes, results in single-site capture at the cathode, but when paced at higher amplitudes, can result in dual-site capture at both cathode and anode. Thus, "virtual" dual-site simultaneous capture can be achieved. Based on the impedance at each electrode and the individual capture thresholds of each unipolar and bipolar configuration, it may cost less battery drain to stimulate the bipolar configuration at higher output rather than using two lower output unipolar pacing pulses. Resultant activation and/or hemodynamics are preferably tested in the unipolar and bipolar configurations in order to ensure comparable outcomes.

At step 442, the system then iteratively tests all remaining Pconfig candidates with various single/multisite configurations, various pacing outputs (amplitude/pulse width), and various interelectrode timing values. The system measures resultant activation/hemodynamics at each and estimates energy cost of each. That is, based on estimated or measured resultant activation and hemodynamics from each pacing configuration whose constituent vectors satisfy the aforementioned factors, and also based on estimated battery drain for each configuration, the remaining non-excluded configurations (single and multisite) are weighed against how well they satisfy the clinician-defined balance between improved cardiac performance and battery longevity. The configurations that satisfy such balance are then preferably tested (not estimated at this point) with multiple fine-tuning iterations so as to incrementally adjust the improvement in performance and the energy savings, while modulating pacing voltage and pulse width and "tweaking" interelectrode timings slightly above and below the estimated optimal values.

The results of these tests are then displayed at step 444 as an ordered list of acceptable/optimal configurations. In other words, each of the acceptable/optimized configurations is ranked based on the clinician-defined balance or bias value and any other a priori constraints. Output of the ranking procedure is either the top "winner" or an ordered list of configurations, with the score according to the balance and, in some examples, also with the individual scores (hemodynamics and longevity). In an embodiment where the procedure is run outside of a clinic, the winning configuration may be programmed or stored for later retrieval. When run in-clinic, the clinician is prompted whether to select the top configuration or another configuration, and can move the aforementioned slider-bar to shift the balance and then see re-computed scores and ranks in order to find a "happy medium" that covers a range of possibilities.

"QuickSense" Sensing Configuration Optimization

Figure 7:
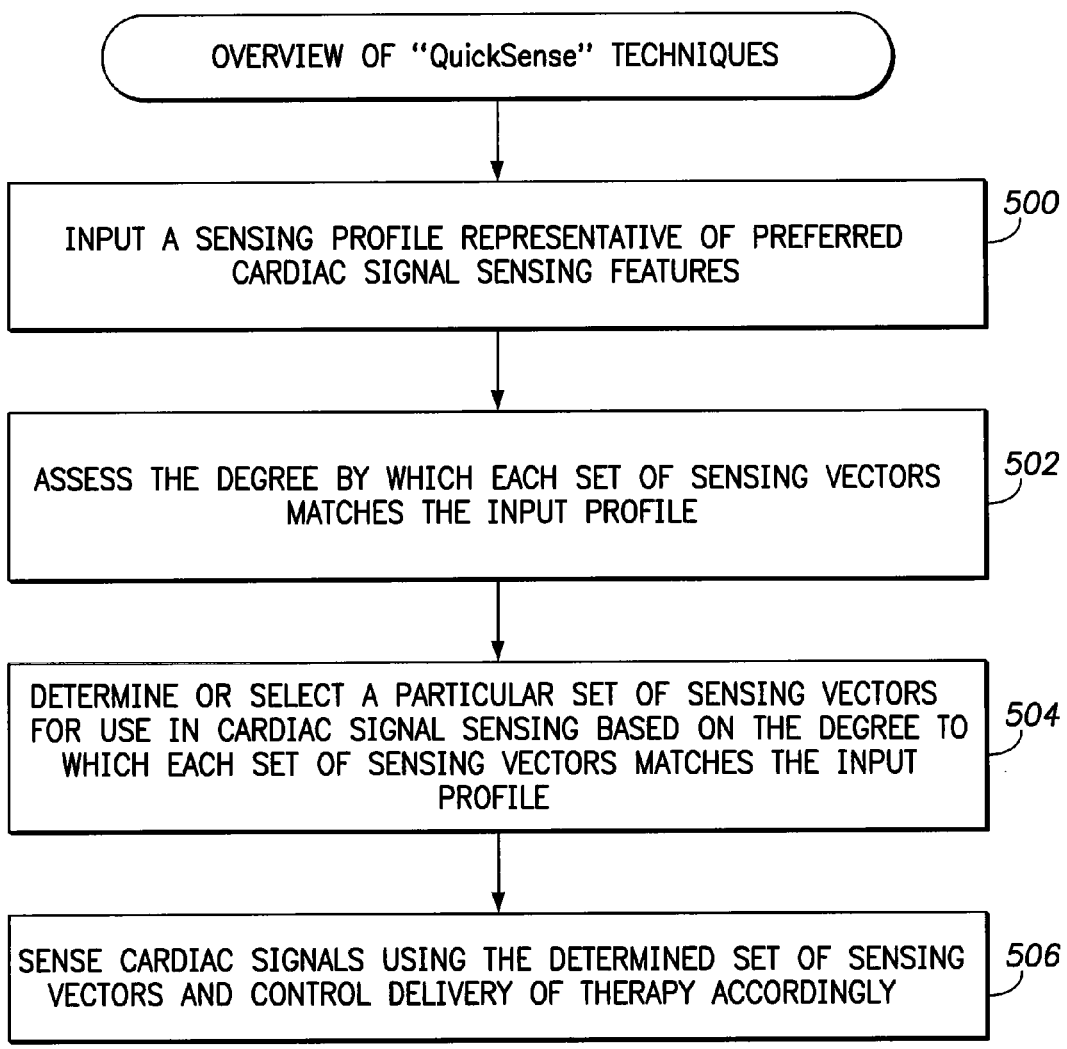
FIG. 7 summarizes a general QuickSense technique for setting cardiac signal sensing configurations based on input sensing profiles, which may be performed by the system of FIG. 1.

FIG. 7 broadly summarizes a general technique that may be exploited by the pacer/ICD and device programmer of FIG. 1 (or other suitably equipped systems) for setting cardiac sensing control parameters based on input profiles. In these and other examples, unless otherwise noted, it is assumed that the techniques are performed under the control of a device programmer in telemetric communication with the pacer/ICD while under clinician supervision. Depending upon the particular features being described, some steps/functions will be performed by the pacer/ICD, others by the device programmer. Collectively, the pacer/ICD and external programmer device are again generally referred to as the system.

As explained above, there are many possible sensing vectors available using quadrapole leads or other MSLV leads. However, despite the number of possible sense vectors, with some pacer/ICD platforms, only up to two vectors can be programmed to record simultaneously. The choice of which vectors are best for sensing depends, at least in part, on electrode position with respect to anatomy and underlying tissues and on what sensed features are of most interest to the clinician. To that end, the QuickSense technique provides for the programming of several "profiles" in order to determine which sensing parameters should be optimized. Some examples herein focus on the limitation of no more than two sense channels; however, these techniques can be applied to an arbitrary number of sense channels.

Beginning at step 500, the system inputs a sensing profile representative of preferred cardiac signal sensing features. This profile may be input, for example, by a clinician using a programmer device or other external system. As will be explained in more detail below, the sensing configuration can specify various desired sensing features, such as V-wave amplitudes, noise levels and/or the presence of far-field signals. At step 502, the system assesses the degree by which each set of sensing vectors matches or achieves the input sensing profile. This may be performed by generating control signals causing the pacer/ICD to sense cardiac signals (such as IEGMs) within the patient using various candidate sensing vectors. The sensed signals are then sent to the device programmer, which analyzes the signals to determine how well the candidate sensing vectors match the desired features of the input profile.

At step 504, the system then selects or determines a particular set of sensing vectors for use in further cardiac sensing based on the degree to which each set of sensing vectors matches the input profile. Typically, the system selects the particular set of sensing vectors that best matches the input profile. However, the clinician can change or supersede the selection based on the clinician's judgment. At step 506, the device programmer then sends control signals to the pacer/ICD to program the pacer/ICD to use the determined or selected set of sensing vectors. The pacer/ICD then senses further cardiac signals within the patient and controls the delivery of therapy based on those signals. In this manner, sensing configurations can be set or optimized based on clinician profiles to achieve desired cardiac signal sensing features within the patient.

Figure 8:
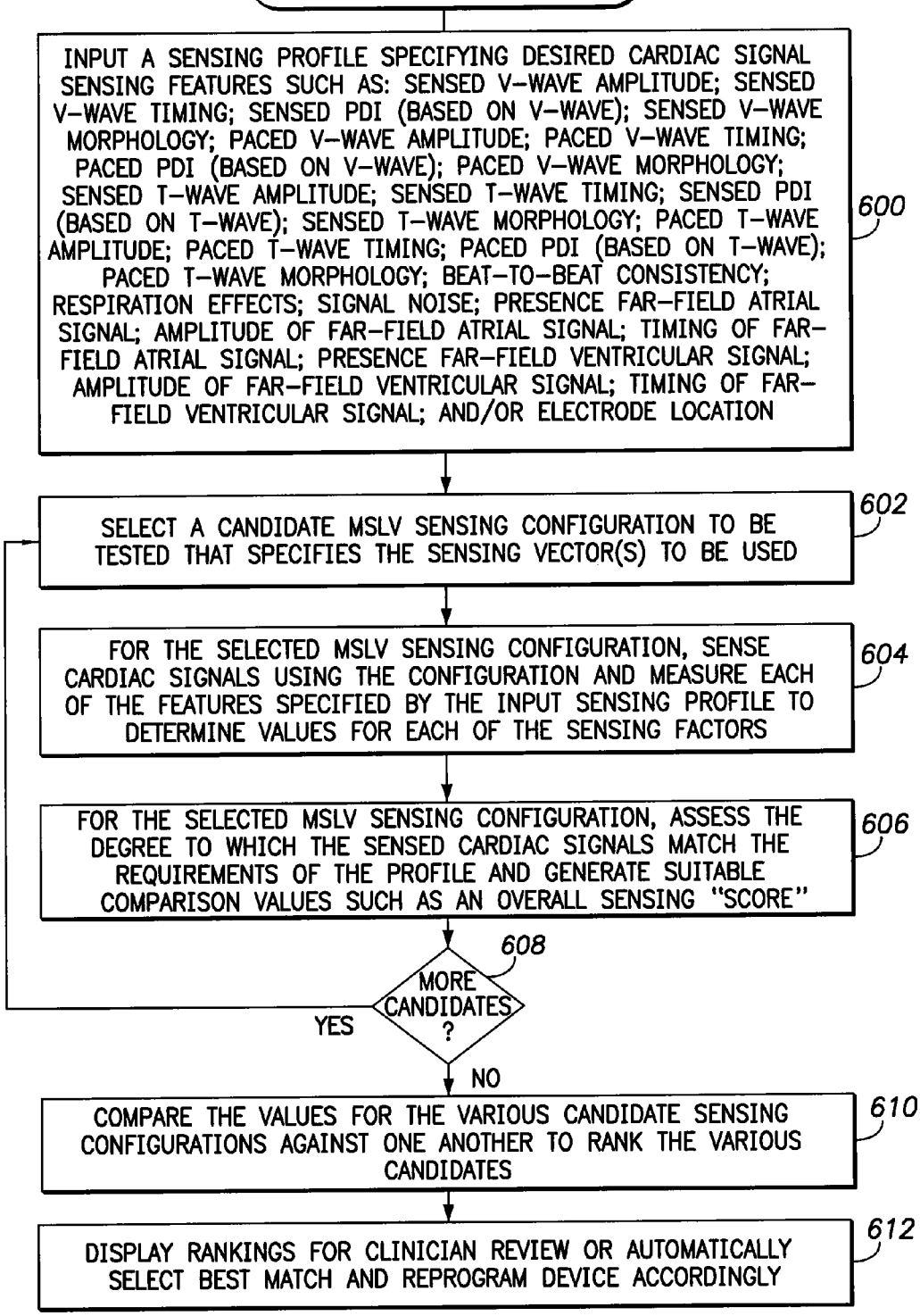
FIG. 8 illustrates an MSLV QuickSense example based on the general QuickSense technique of FIG. 7.

FIG. 8 provides further details pertaining to an MSLV implementation wherein the QuickSense techniques operate to identify an MSLV sensing configuration that most closely matches a sensing profile input by a clinician. Beginning at step 600, the system inputs a sensing profile specifying desired cardiac signal sensing features such as: sensed V-wave amplitude; sensed V-wave timing; sensed PDI (based on V-wave); sensed V-wave morphology; paced V-wave amplitude; paced V-wave timing; paced PDI (based on V-wave); paced V-wave morphology; sensed T-wave amplitude; sensed T-wave timing; sensed PDI (based on T-wave); sensed T-wave morphology; paced T-wave amplitude; paced T-wave timing; paced PDI (based on T-wave); paced T-wave morphology; beat-to-beat consistency; respiration effects; signal noise; presence far-field atrial signals; amplitudes of far-field atrial signals; timing of far-field atrial signals; presence far-field ventricular signals; amplitudes of far-field ventricular signals; timing of far-field ventricular signals; and/or electrode location(s). Relative weights for these parameters can be input as well.

At step 602, the system selects a candidate MSLV sensing configuration to be tested from among a set of possible MSLV sensing configurations that specifies: the particular MSLV sensing vector(s) to be used and, in some implementations, the particular sensing channels to be used along with the set of sensing vectors. In this regard, in some embodiments, there are two "sense amps" as well as an "ischemia channel" and a few "wideband" channels on board the implanted device; the choice of vectors and channels only affects what the device "sees." It may be important in some cases, in addition to sensing cardiac signals with the selected MSLV sensing configuration, to additionally or alternatively "estimate" the sensed signal based on a previously recorded signal from the same, similar, or different sense configuration. For example, a monomorphic VT that is stored by the device "Event Triggers" might be "played back" to estimate how that VT may have looked had a different sense configuration been selected. This type of computation would preferably be handled by the programmer but, in at least some examples, might be performed by the implanted device if properly equipped.

At step 604, for the selected MSLV sensing configuration, the system senses cardiac signals using the configuration and measures each of the features specified by the input sensing profile to determine values for each of the sensing factors. Typically, this is performed by sending suitable programming commands from the device programmer to the pacer/ICD that control the pacer/ICD to sense sample cardiac signals using the selected sensing configuration. The pacer/ICD then sends the sample signals to the device programmer, which analyzes the sample signals to measure or otherwise quantify the various sensing factors.

At step 606, for the currently-selected MSLV sensing configuration, the device programmer assesses the degree to which the sensed cardiac signals match the requirements of the sensing profile and generates suitable comparison values, such as an overall sensing "score." Assuming there are more sensing configurations to be tested, as determined at step 608, the system returns to step 602 to select a different sensing configuration and the assessment procedure is repeated. (Various "shortcut" techniques for discussed below for reducing the total number of sensing tests.)

Once the last of the candidates has been tested, processing proceeds to step 610 wherein the system compares the values or scores for the various candidate sensing configurations against one another and ranks the values based on the degree of match. At step 612, the device programmer displays the rankings for clinician review or, in some implementations, the system automatically selects a best match and reprograms the pacer/ICD accordingly. Clinician review is preferred. However, in some circumstances, such as if there is a problem with a current MSLV sensing configuration (due, e.g., to a failure of a given electrode of a lead or due to lead dislodgement), it might be appropriate for the pacer/ICD to automatically perform the sensing assessment and to automatically switch to a different sensing configuration to ensure proper ongoing pacing therapy, pending subsequent clinician review. That is, the device may automatically perform the steps if it detects some failure in the presently-selected sense configuration. Alternately, it might revert to the previously-determined "next best" sense configuration that would avoid the failure.

Figure 9:
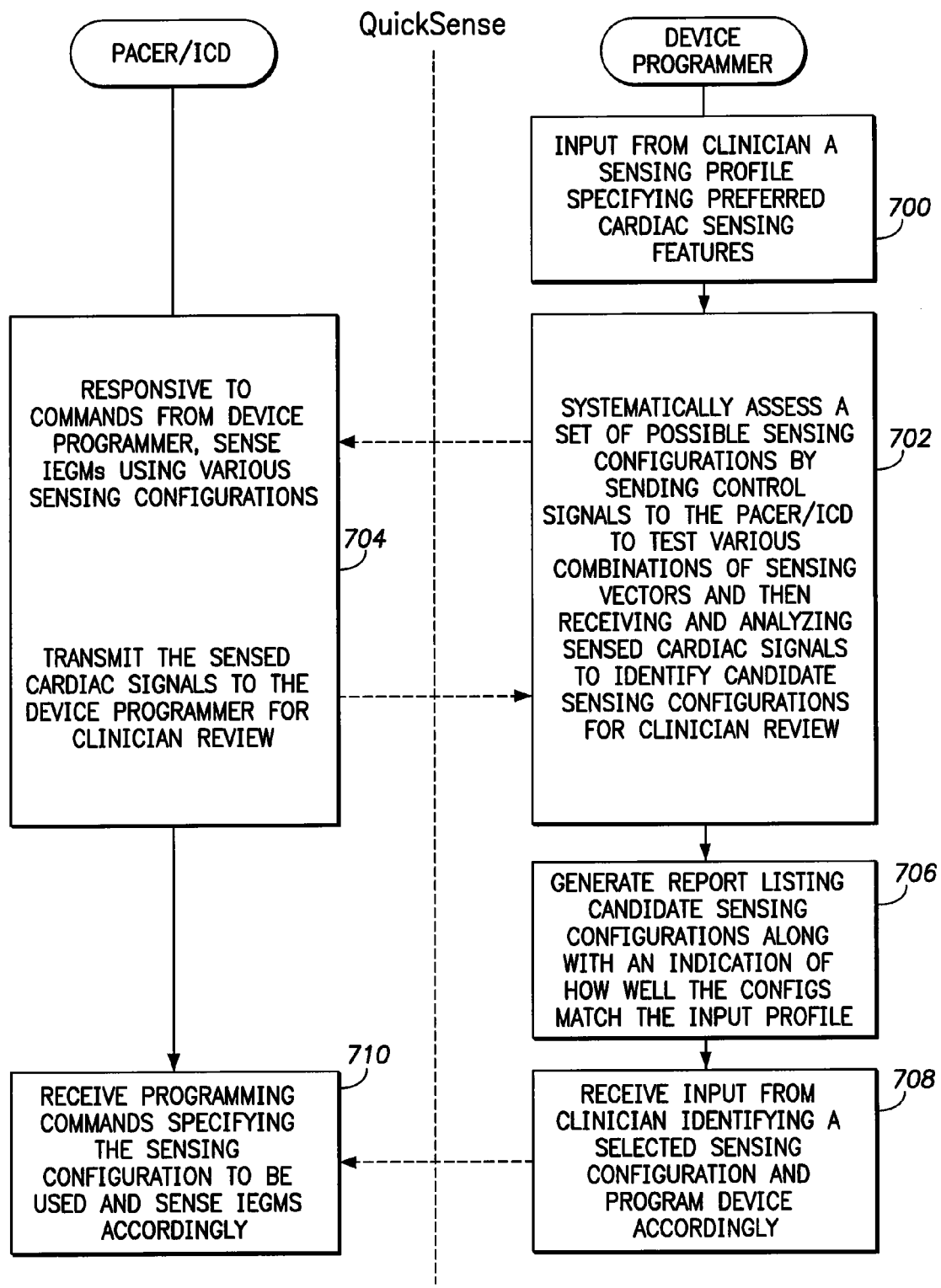
FIG. 9 is a flowchart illustrating an exemplary implementation of the MSLV QuickSense technique of FIG. 8 wherein the implanted device operates in conjunction with an external programmer system.

Turning now to FIG. 9, QuickSense techniques will be described with reference to an in-clinic example under clinician supervision. At step 700, the external device programmer inputs from the clinician a set of sensing profiles specifying preferred cardiac sensing features, as well as the relative weights of the features. Exemplary sensing features are listed above. Particular features may be input or selected via appropriate graphical displays generated by the device programmer. For example, the clinician might select particular features from a list of features, by using a mouse controller or other suitable input device, so as to create a custom profile. The clinician can then enter particular numerical values, where appropriate, specifying individual features, such as minimum values for V-wave amplitudes or maximum values for noise levels. In other examples, a set of predetermined sensing profiles are stored in the device programmer and the clinician merely selects among the predetermined profiles.

Once the clinician has specified a sensing profile, he or she initiates an automatic sensing optimization procedure at step 702. The device programmer then initiates a series of sensing tests intended to identify one or more sensing configurations that satisfy the profile criteria entered by the clinician. During the sensing test, an indication can be provided on the display screen as to the completion status of the test. This indication may be determined based on the total number of sensing configurations to be tested as compared to the number of tests already completed.

More specifically, at step 702, the device programmer systematically assesses a set of possible sensing configurations by sending control signals to the pacer/ICD to test various combinations of sensing vectors and then receiving and analyzing sensed cardiac signals to rank candidate sensing configurations for clinician review. To this end, a series of sensing tests are performed where the programmer sends control signals to the pacer/ICD to program the device to temporarily sensing signals using a given sensing configuration. These tests are performed at step 704 wherein, responsive to commands from the device programmer, the pacer/ICD senses IEGMs in accordance with test sensing configurations while measuring cardiac signal parameters such as signals amplitudes; noise levels; etc. Upon completing a test with a given sensing configuration, the pacer/ICD transmits the sensed IEGMs and the measured values to the device programmer for storage and analysis therein and for subsequent clinician review.

The procedure of steps 702 and 704 continues until all sensing configurations and/or combinations of configurations to be tested by the pacer/ICD and results compiled. Various techniques for reducing the total number of sensing tests to be performed will be described below. For each test, scores are calculated by the device programmer that indicative the extent to which the given sensing configuration meets the sensing profile originally input by the clinician.

At step 706, the device programmer then generates a report listing candidate sensing configurations that generally satisfy the input sensing profile, along with a display of sensed IEGMs and the aforementioned scores. By clicking or touching the display screen, the clinician can call up additional details regarding the sensing configurations, including the results of the sensing tests (including, e.g., lists of the particular sensing profile factors measured during the test, as well as displays of IEGMs, etc.) At step 708, the device programmer receives input from clinician specifying a selected sensing configuration and then programs the pacer/ICD accordingly by transmitting suitable control signals. At step 710, the pacer/ICD receives the programming commands specifying the sensing configuration to be used and then begins sensing cardiac signals using that new configuration and delivering pacing therapy accordingly.

Figures 1, 10:
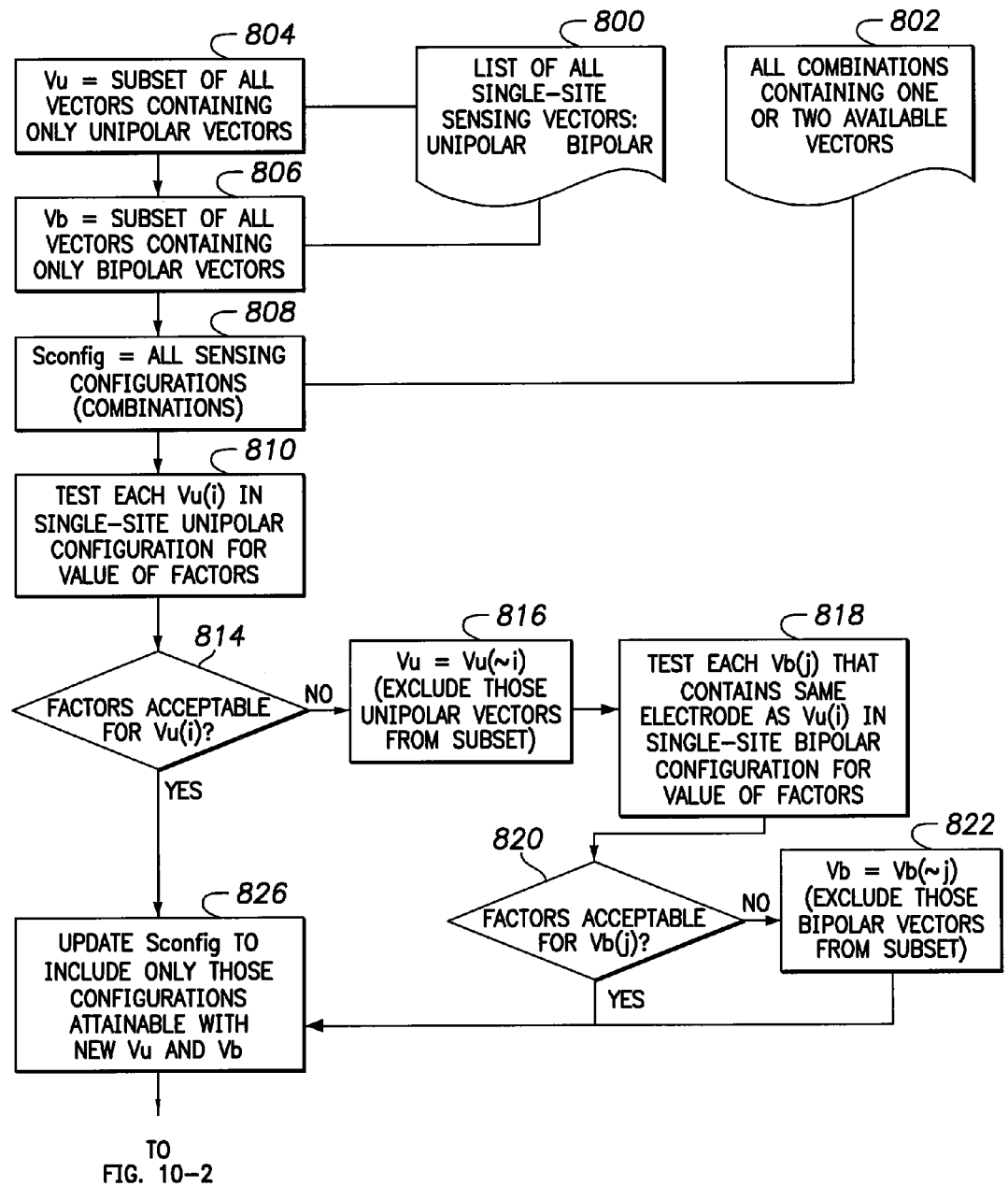
FIG. 10 illustrates a more detailed MSLV QuickSense example, also in accordance with the general technique of FIG. 7, which particularly illustrates various sensing optimization "short cuts"
Figures 2, 10:
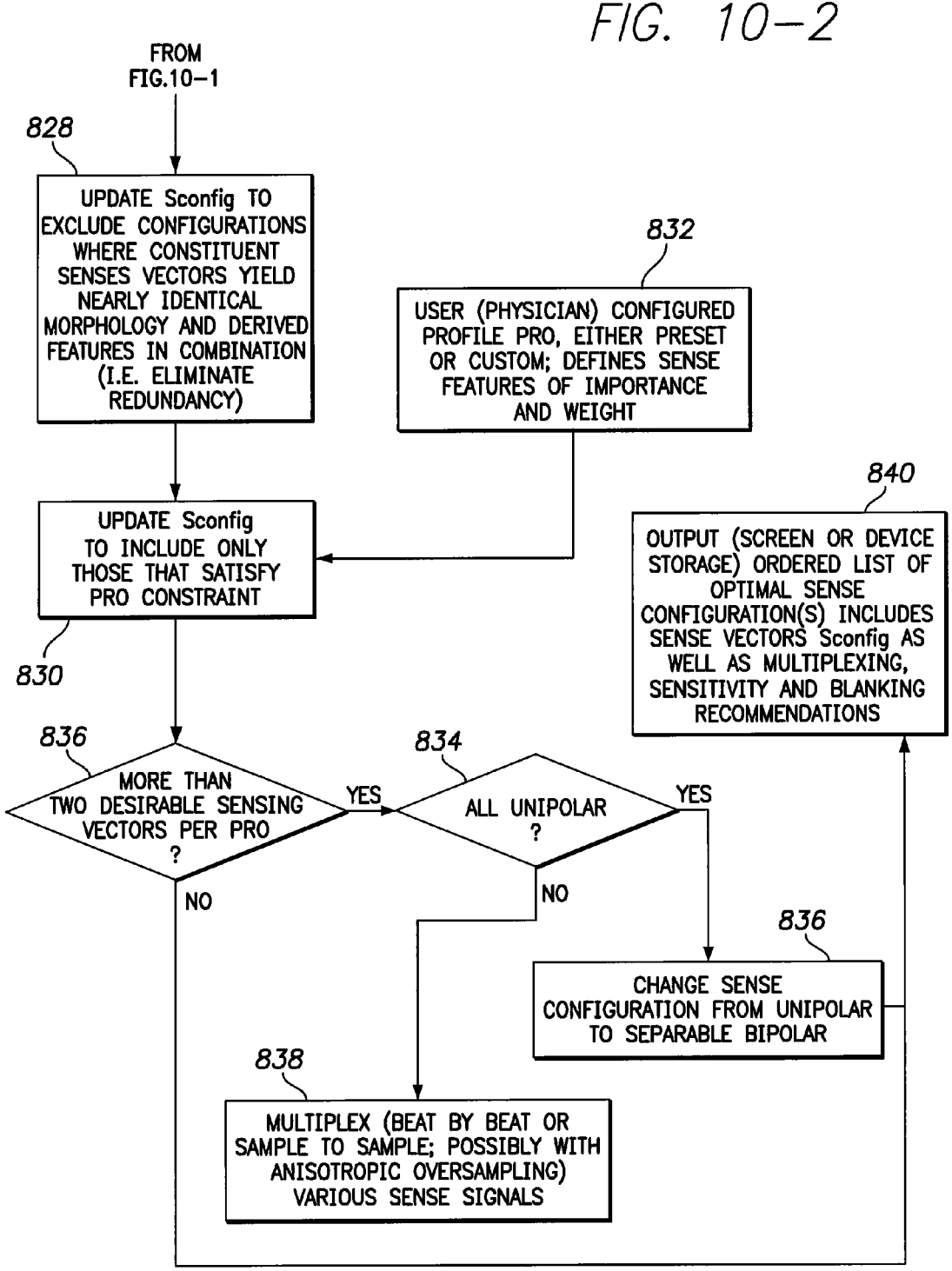

In FIG. 10, still further details pertaining to an exemplary QuickSense implementation will be described, wherein various shortcuts are illustrated. With this technique, all available unipolar and bipolar sensing configurations are recorded over several cardiac cycles to determine value for the sensing factors for each sensing vector. The values of the sensing factors are temporarily stored for use with computing of the profile score for each sensing vector.

Beginning at step 800, a list of all single-site unipolar and bipolar sensing vectors for the implanted pacer/ICD is retrieved from memory by the external programmer. At step 802, the system identifies all combinations of sensing vectors that contain one or two available vectors. One combination might be two vector combination where a first IEGM is sensed bipolar Tip-R1 and a second IEGM is sensed bipolar R1-R3. At step 804, the system generates an array Vu that represents the subset of all sensing vectors containing only unipolar vectors. At step 806, the system generates a second array Vb that represents the subset of all sensing vectors containing bipolar vectors. At step 808, the system generates an array Sconfig that represents all sensing configurations, i.e. all combinations retrieved at step 802. Note that Vb and Vu for use with QuickSense can differ from the corresponding arrays used for QuickStim.

At step 810, the system tests each Vu(i) in single-site unipolar configuration to determine values of each of the various single-site sensing profile factors, such as those listed in step 600 of FIG. 8. At step 814, the system evaluates the factors for Vu(i) to determine if the factors are acceptable. Depending upon the particular sensing factor, this can involve comparing the factor against one or more threshold values representative of acceptable values. Assuming that at least some of the sensing factors are found to be unacceptable for a given unipolar vector (i), then at step 816, the system excludes the unipolar vector from further consideration. This can greatly reduce the total number of sensing tests that need to be performed and hence represents one of the aforementioned shortcuts.

At step 818, the system then tests each Vb(j) that contains the same electrode as Vu(i) in single-site bipolar configuration to determine values for the aforementioned sensing factors. At step 820, the system evaluates the factors for Vb(j) to determine if the factors are acceptable. Assuming that at least some of the factors are found to be unacceptable for a given bipolar vector (j), then at step 822, the system excludes the bipolar vector from further consideration. This likewise can reduce the total number of sensing tests that need to be performed.

Processing then proceeds to step 826 where the system updates Sconfig to include only those configurations attainable with new Vu and Vb (i.e. while excluding any configuration incorporating an excluded vector.) At step 828, the system then updates Sconfig to exclude sensing configurations whose constituent sense vectors yield nearly identical morphology and derived features in combination (i.e. this step eliminates certain redundancies.) Thereafter, at step 830, the system updates Sconfig to include only those combinations that satisfy any clinician or physician constraints input at step 832. That is, at step 832, the User (physician or clinician) inputs a configuration Profile PRO, either preset or custom, which defines sense features of importance and their respective weights.

At step 836, a determination is made whether there are more than two desirable sensing vectors per PRO (i.e. whether two more sensing configurations are acceptable in view of the input profile.) If so, then the system, at step 834, determines whether the acceptable sensing vectors are all unipolar. If so, then the system, at step 836, changes the sense configuration from unipolar to separable bipolar configurations. If not all unipolar then, at step 838, the system sets up virtual sensing channels that multiplex (beat-by-beat or sample-by-sample with possible anisotropic oversampling) various sense signals. This will be described in more detail below with reference to FIG. 11.

Eventually, processing continues to step 840 wherein the results of the various sense tests are displayed as an ordered list of acceptable/optimal sensing configurations. Each of the acceptable/optimized sensing configurations is ranked based on the clinician-defined profile (PRO). Output of the ranking procedure is either the top "winner" or an ordered list of configurations, with the score according to degree to which the configurations matches the profile. In the case of in-clinic follow-up, the ordered winners can be displayed on the programmer screen to allow the user to select or customize a configuration. In the case of device-based auto-sense-configuration, the winner can be stored for notification at the next follow-up or Merlin@home transmission and/or permanently programmed.

In other words, at step 840, the system provides recommendations as to the sense vectors to be used. For the case of a device with two sense channels, the recommendation includes which sense vectors to configure on each of the two available channels, what sensitivity levels and blanking/refractory periods should be set, whether one or more channels should be multiplexed, and if the multiplexing should include anisotropic oversampling. A "Details" screen may be provided that shows the user what the sense channel recordings will look like (based on the test sense data) and what confidence/risks are involved when using the recommended vectors in relation to the profile. For example, if sensitivity is recommended to be set at 12 mV, an estimate is provided of what might happen (physiologically and/or clinically) to cause inappropriate detection of tachyarrhythmia due to, for example, T-wave oversensing, or what might result in inappropriate pace into refractory tissue due to undersensed V wave. The system can also provide an indication, for example, of how confidently MSLV-AutoCapture could operate, given multiplexing or anisotropic oversampling of two or more MSLV electrodes on a quadrapole lead.

Typically, the physician or clinician will have in mind the most-likely risks for a given patient. For example, some ischemic patients will be at higher risk for VT/VF episodes, while DCM patients may be at greater risk for loss of BiV capture due to intrinsic fusion resulting in deteriorating hemodynamics. As such, the "optimal" sensing configurations for these two patients may differ. This is one of the advantages when using the QuickSense profiles. The profiles offer the user a pre-set scheme for weighing the many factors that go into optimizing the sensing configuration in MSLV/Quadrapole platform. Thus, all factors can be collected/measured during the sense test for each sense vector, and the choice of sensing profile determines how to weigh the factor values to yield a final QuickSense score. Preferably, the system offers pre-set profiles set to: maximize arrhythmia detection; ensure maximum BiV pacing; optimize VV and intra-V timing intervals or activity-response slope; allow for diagnostics such as evoked response, etc. These profiles may be determined in advance based, e.g., on the analysis of clinical data.

Figure 11:
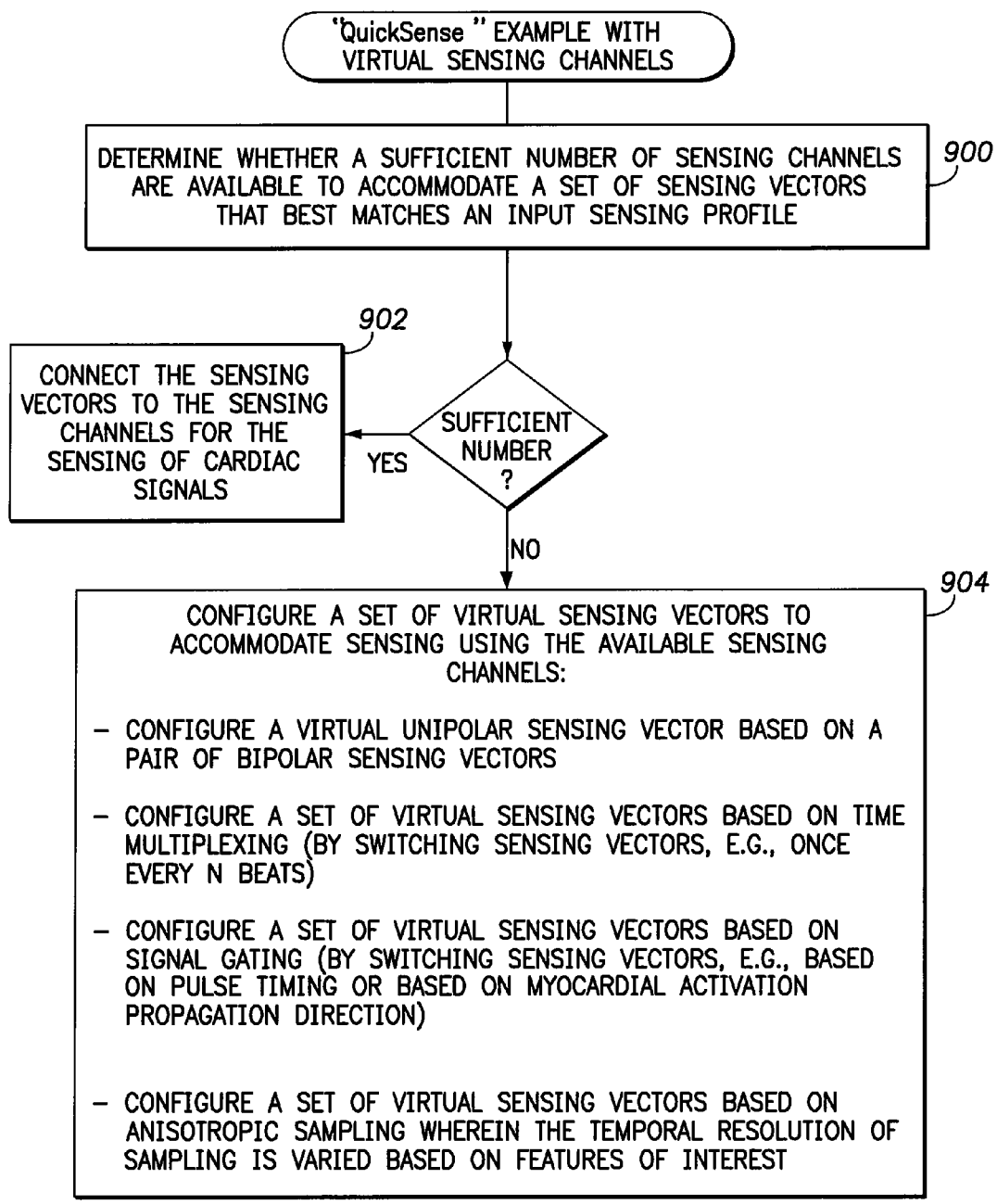
FIG. 11 is a flowchart illustrating the use of virtual sensing channels for use with the technique of FIG. 7.

Turning now to FIG. 11, virtual sensing channels will be more fully described. Based on the sensing factor values and the sensing profile chosen, it may be the case that one or two sense vectors will satisfy the needs of the stored/diagnostic data collection. In other cases, three or more sense vectors might be necessary. As noted, in at least some devices, only two physical sensing channels are available for recording IEGMs. Accordingly, it may be useful to establish virtual sensing channels to permit multiple channels of IEGMs to be recorded using fewer physical channels. To this end, at step 900, the system determines whether a sufficient number of physical sensing channels are available to accommodate a set of sensing vectors that best matches an input sensing profile. If so, then, at step 902, the system connects the sensing vectors to the physical sensing channels for sensing cardiac signals. If not, then step 904 is instead performed wherein the system configures a set of virtual sensing vectors to accommodate sensing using the available physical sensing channels using one or more of the following:

- configure a virtual unipolar sensing vector based on a pair of bipolar sensing vectors
- configure a set of virtual sensing vectors based on time multiplexing (by switching sensing vectors, e.g., once every n beats)
- configure a set of virtual sensing vectors based on signal gating (by switching sensing vectors based, e.g., on pulse timing or based on myocardial activation propagation direction)
- configure a set of virtual sensing vectors based on anisotropic sampling wherein the temporal resolution of sampling is varied based on features of interest In this regard, if all of the desired sense vectors are unipolar, then separable combinations of the unipolar vectors to create exactly two bipolar vectors with the constituent electrodes is recommended. For example, if the optimal sense vectors are Tip-Case, R1-Case, and R2-Case, then in order to record all three on no more than two sense channels, the device programmer can program the pacer/ICD to record Tip-R1 and R2-R1 as bipolar sense vectors. The R1 "virtual unipolar" signal can then be separated as the common-mode signal, while the Tip "virtual unipolar" and R2 "virtual unipolar" signals are separated by common-mode rejection or subtraction of the R1 virtual unipolar signal. If some of the desired sense vectors are bipolar (or there are too many desired sense vectors to create two separable bipolar channels), then a sense multiplexing scheme is recommended in which each of the two available sense channels alternate among the various desired sense vectors on a beat-by-beat basis or on a sample-by-sample basis. For example, if Tip-R1, R2-Case, and R3-Coil are all desirable sense vectors based on the sensing factors and profile, then one sense channel may be programmed to alternate each beat or every $2^{nd}$ or $3^{rd}$ beat between R2-Case and R3-Coil (or each sample may alternate as such.) The beats or samples are associated in a known scheme with the particular vector in which they originated, such that the microprocessor electronics of the device can later separate the signals for recording or other processing.

Insofar as gating is concerned, in the previous example, if R2 is also a paced electrode, then the shared (multiplexed) sense channel can be switched to R3 during and immediately following the delivery of the R2 pacing pulse, as the pacing pulse would require the blanking of the R2 sense anyway. Alternately, if activation has previously been sensed to travel in a particular direction within the heart given the current interelectrode timing (for example, typically R2 senses activation 20 ms before R3 senses it, and R2 is typically 10 ms after measured Tip-R1 activation) then samples can be alternated "several-to-one" (instead of one-to-one) at the electrode of interest, where R2 sense would be sampled, in one example, 4 times for every 1 sample of R3 between 8-14 ms after Tip-R1 sense, then 1:1 from 14-27 ms after Tip-R1, then 1:4 (oversample R3) from 28-106 ms after Tip-R1. In this manner, features of interest on a particular sense vector can be recorded at higher temporal resolution while still monitoring other sense vectors for aberrant activity (i.e. if the device detects an unusually early activation during the "undersampled" portion on R3, then the next beat can be switched back to the 1:1 sampling scheme), and then features of interest on a different sense vector can be recorded on the same channel. The method where temporal resolution is selectively controlled is referred to as "anisotropic oversampling."

Thus, a variety of exemplary QuickStim and QuickSense optimization techniques have been described. The techniques can be used, where appropriate, in conjunction with other optimization procedures. See, for example, U.S. patent application Ser. No. 11/750,153, filed May 17, 2007, entitled "Expedited Set-Up of Multi-Electrode Lead (MEL)".

Note that, in addition to determining and using the aforementioned MSLV pacing and sensing configurations, the system can also determine and use various interelectrode delays (set as described in the above-cited patent application to Ryu et al.), as well as various AV/PV pacing delays and VV pacing delays.

The following patents and patent applications set forth various systems and methods for allowing a pacemaker, ICD, CRT device or other cardiac stimulation device to determine and/or adjust AV/PV/VV pacing delays so as to help maintain the pacing delays at optimal values: U.S. patent application Ser. No. 10/703,070, filed Nov. 12, 2003, entitled "Methods for Ventricular Pacing", now abandoned; U.S. patent application Ser. No. 10/974,123, filed Oct. 26, 2004 A03P1074US01), now abandoned; U.S. patent application Ser. No. 10/986,273, filed Nov. 10, 2004, now U.S. Pat. No. 7,590,446; U.S. patent application Ser. No. 10/980,140, filed Nov. 1, 2004, now abandoned; U.S. patent application Ser. No. 11/129,540, filed May 13, 2005, now abandoned; U.S. patent application Ser. No. 11/952,743, filed Dec. 7, 2007. See, also, U.S. patent application Ser. No. 12/328,605, filed Dec. 4, 2008, entitled "Systems and Methods for Controlling Ventricular Pacing in Patients with Long Intra-Atrial Conduction Delays"; U.S. patent application Ser. No. 12/132,563, filed Jun. 10, 2008, entitled "Systems and Methods for determining Intra-Atrial Conduction Delays using Multi-Pole Left Ventricular Pacing/Sensing Leads", now U.S. Pub. App. 2009/0299423A1; and U.S. patent application Ser. No. 12/507,679, filed Jul. 22, 2009, entitled "Systems and Methods for Optimizing Ventricular Pacing Delays During Atrial Fibrillation". See, further, U.S. Pat. No. 7,248,925, to Bruhns et al., entitled "System and Method for Determining Optimal Atrioventricular Delay based on Intrinsic Conduction Delays."

In particular, techniques are set forth within at least some of these patent documents for exploiting various inter-atrial and interventricular conduction delays to determine preferred or optimal AV/PV/VV pacing delays. Techniques are also set forth for exploiting the VV delays to determine which ventricles should be paced—the left ventricle (LV), the right ventricle (RV), both ventricles, or neither, and in which order. Note that at least some of the techniques are implemented within the "QuickOpt" systems of St. Jude Medical, wherein QuickOpt is a trademark. QuickStim and QuickSense may also be regarded as trademarks.

Note also that, in the examples described herein, the multi-pole ventricular lead is an LV lead, but it should be understood that aspects of the invention are applicable to multi-pole RV leads. Indeed, at least some of the techniques described herein are also generally applicable to implementations wherein both the LV and RV have multi-pole leads. Still further, the techniques are applicable to multi-pole atrial leads, implanted on or in either the RA or the LA. As such, at least some of the techniques described herein are generally applicable to optimizing pacing and sensing configurations as applied leads implanted on or in any of the four chambers of the heart.

Also, it should be understood that the optimal sensing/pacing combinations/permutations described herein are not necessarily absolutely optimal in a given quantifiable or mathematical sense. As can be appreciated, what constitutes an "optimal" pacing or sensing configuration depends on the criteria used for judging the resulting pacing or sensing performance, which can be subjective in the minds of some clinicians. The configurations determined by the techniques described herein represent, at least, "preferred" configurations. Clinicians may choose to adjust or alter the selection via device programming for particular patients, at their discretion.

Although primarily described with respect to examples having a pacer/ICD, other implantable medical devices may be equipped to exploit the techniques described herein such as CRT devices and CRT-D devices (i.e. a CRT device also equipped to deliver defibrillation shocks) or CRT-P devices (i.e. a CRT device also equipped to deliver pacing.) For the sake of completeness, an exemplary pacer/ICD will now be described, which includes components for performing at least some of the functions and steps already described.

Exemplary Pacer/ICD

Figure 12:
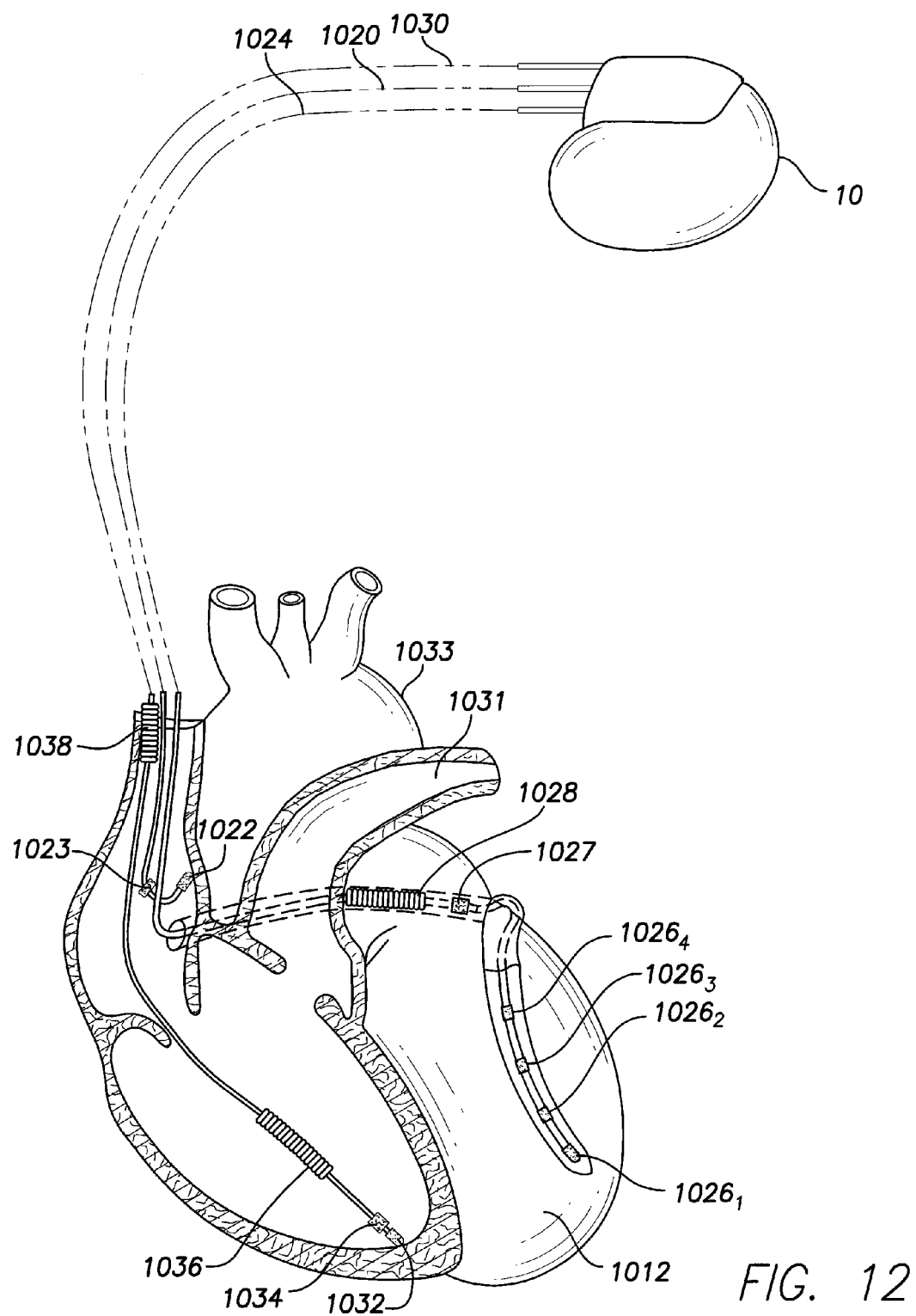
FIG. 12 is a simplified, partly cutaway view, illustrating the implantable device of FIG. 1 along with at set of leads implanted into the heart of the patient.
Figure 13:
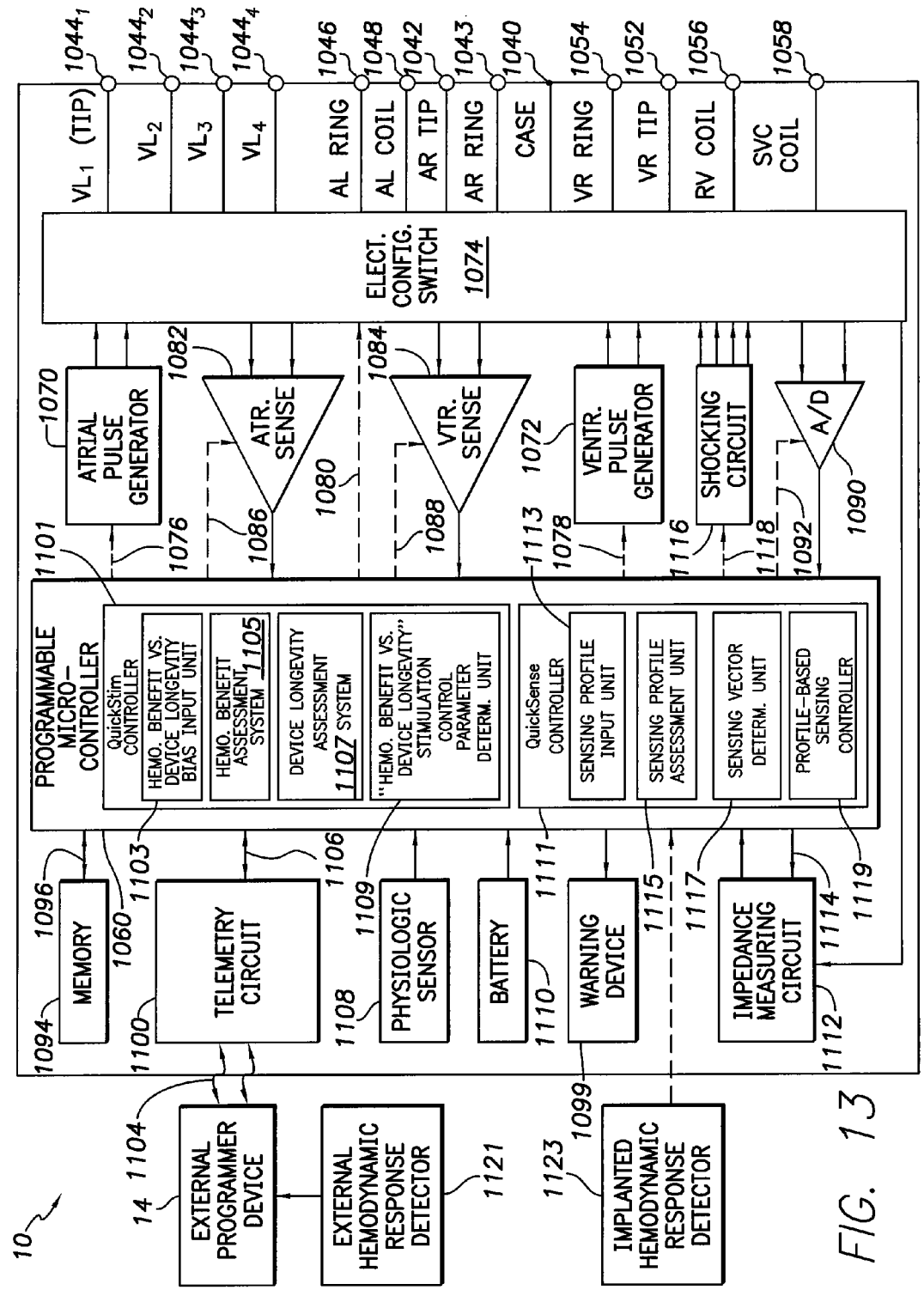
FIG. 13 is a functional block diagram of the pacer/ICD of FIG. 12, illustrating basic circuit elements that provide cardioversion, defibrillation and/or pacing stimulation in the heart, particularly illustrating on-board optimization components for use with the techniques of FIGS. 2-12.

With reference to FIGS. 12 and 13, a description of an exemplary pacer/ICD will now be provided. FIG. 12 provides a simplified block diagram of the pacer/ICD, which is a dual-chamber stimulation device capable of treating both fast and slow arrhythmias with stimulation therapy, including cardioversion, defibrillation, and pacing stimulation, and also capable of setting and using VV pacing delays, as discussed above. To provide other atrial chamber pacing stimulation and sensing, pacer/ICD 10 is shown in electrical communication with a heart 1012 by way of a left atrial lead 1020 having an atrial tip electrode 1022 and an atrial ring electrode 1023 implanted in the atrial appendage. Pacer/ICD 10 is also in electrical communication with the heart by way of a right ventricular lead 1030 having, in this embodiment, a ventricular tip electrode 1032, a right ventricular ring electrode 1034, a right ventricular (RV) coil electrode 1036, and a superior vena cava (SVC) coil electrode 1038. Typically, the right ventricular lead 1030 is transvenously inserted into the heart so as to place the RV coil electrode 1036 in the right ventricular apex, and the SVC coil electrode 1038 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a multi-pole LV lead 1024 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary LV lead 1024 is designed to receive atrial and ventricular cardiac signals and to deliver left ventricular pacing therapy using a set of four left ventricular electrodes $1026_1$, $1026_2$, $1026_3$, and $1026_4$ (thereby providing a Quadrapole lead), left atrial pacing therapy using at least a left atrial ring electrode 1027, and shocking therapy using at least a left atrial coil electrode 1028. The $1026_1$ LV electrode may also be referred to as a "tip" or "distal" LV electrode. The $1026_4$ LV electrode may also be referred to as a "proximal" LV electrode. In other examples, more or fewer LV electrodes are provided. Although only three leads are shown in FIG. 12, it should also be understood that additional leads (with one or more pacing, sensing and/or shocking electrodes) might be used and/or additional electrodes might be provided on the leads already shown, such as additional electrodes on the RV lead.

A simplified block diagram of internal components of pacer/ICD 10 is shown in FIG. 13. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. The housing 1040 for pacer/ICD 10, shown schematically in FIG. 13, is often referred to as the "can", "case" or "case electrode" and may be programmably selected to act as the return electrode for all "unipolar" modes. The housing 1040 may further be used as a return electrode alone or in combination with one or more of the coil electrodes, 1028, 1036 and 1038, for shocking purposes. The housing 1040 further includes a connector (not shown) having a plurality of terminals, 1042, 1043, $1044_1$-$1044_4$, 1046, 1048, 1052, 1054, 1056 and 1058 (shown schematically and, for convenience, the names of the electrodes to which they are connected are shown next to the terminals). As such, to achieve right atrial sensing and pacing, the connector includes at least a right atrial tip terminal ($A_R$ TIP) 1042 adapted for connection to the atrial tip electrode 1022 and a right atrial ring ($A_R$ RING) electrode 1043 adapted for connection to right atrial ring electrode 1023. To achieve left chamber sensing, pacing and shocking, the connector includes a left ventricular tip terminal ($VL_1$ TIP) $1044_1$ and additional LV electrode terminals $1044_2$-$1044_4$ for the other LV electrodes of the Quadrapole LV lead.

The connector also includes a left atrial ring terminal ($A_L$ RING) 1046 and a left atrial shocking terminal ($A_L$ COIL) 1048, which are adapted for connection to the left atrial ring electrode 1027 and the left atrial coil electrode 1028, respectively. To support right chamber sensing, pacing and shocking, the connector further includes a right ventricular tip terminal ($V_R$ TIP) 1052, a right ventricular ring terminal ($V_R$ RING) 1054, a right ventricular shocking terminal ($V_R$ COIL) 1056, and an SVC shocking terminal (SVC COIL) 1058, which are adapted for connection to the right ventricular tip electrode 1032, right ventricular ring electrode 1034, the $V_R$ coil electrode 1036, and the SVC coil electrode 1038, respectively. Although not shown in the figure, additional terminals can be provided to accommodate any sub-Q electrodes that might be provided as part of the implantable system.

At the core of pacer/ICD 10 is a programmable microcontroller 1060, which controls the various modes of stimulation therapy. As is well known in the art, the microcontroller 1060 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 1060 includes the ability to process or monitor input signals (data) as controlled by a program code stored in a designated block of memory. The details of the design and operation of the microcontroller 1060 are not critical to the invention. Rather, any suitable microcontroller 1060 may be used that carries out the functions described herein. The use of microprocessor-based control circuits for performing timing and data analysis functions are well known in the art.

As shown in FIG. 13, an atrial pulse generator 1070 and a ventricular pulse generator 1072 generate pacing stimulation pulses for delivery by the right atrial lead 1020, the right ventricular lead 1030, and/or the LV lead 1024 via an electrode configuration switch 1074. It is understood that in order to provide stimulation therapy in each of the four chambers of the heart, the atrial and ventricular pulse generators, 1070 and 1072, may include dedicated, independent pulse generators, multiplexed pulse generators or shared pulse generators. The pulse generators, 1070 and 1072, are controlled by the microcontroller 1060 via appropriate control signals, 1076 and 1078, respectively, to trigger or inhibit the stimulation pulses.

The microcontroller 1060 further includes timing control circuitry (not separately shown) used to control the timing of such stimulation pulses (e.g., pacing rate, AV delay, atrial interconduction (inter-atrial) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 1074 includes a plurality of switches for connecting the desired electrodes to the appropriate I/O circuits, thereby providing complete electrode programmability. Accordingly, the switch 1074, in response to a control signal 1080 from the microcontroller 1060, determines the polarity of the stimulation pulses (e.g., unipolar, bipolar, combipolar, etc.) by selectively closing the appropriate combination of switches (not shown) as is known in the art. The switch also switches among the various LV electrodes.

Atrial sensing circuits 1082 and ventricular sensing circuits 1084 may also be selectively coupled to the right atrial lead 1020, LV lead 1024, and the right ventricular lead 1030, through the switch 1074 for detecting the presence of cardiac activity in each of the four chambers of the heart. Accordingly, the atrial (ATR. SENSE) and ventricular (VTR. SENSE) sensing circuits, 1082 and 1084, may include dedicated sense amplifiers, multiplexed amplifiers or shared amplifiers. The switch 1074 determines the "sensing polarity" of the cardiac signal by selectively closing the appropriate switches, as is also known in the art. In this way, the clinician may program the sensing polarity independent of the stimulation polarity. Each sensing circuit, 1082 and 1084, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 1082 and 1084, are connected to the microcontroller 1060 which, in turn, are able to trigger or inhibit the atrial and ventricular pulse generators, 1070 and 1072, respectively, in a demand fashion in response to the absence or presence of cardiac activity in the appropriate chambers of the heart.

For arrhythmia detection, pacer/ICD 10 utilizes the atrial and ventricular sensing circuits, 1082 and 1084, to sense cardiac signals to determine whether a rhythm is physiologic or pathologic. As used in this section "sensing" is reserved for the noting of an electrical signal, and "detection" is the processing of these sensed signals and noting the presence of an arrhythmia. The timing intervals between sensed events (e.g., AS, VS, and depolarization signals associated with fibrillation which are sometimes referred to as "F-waves" or "Fib-waves") are then classified by the microcontroller 1060 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 1090. The data acquisition system 1090 is configured to acquire intracardiac electrogram signals, convert the raw analog data into a digital signal, and store the digital signals for later processing and/or telemetric transmission to an external device 1102. The data acquisition system 1090 is coupled to the right atrial lead 1020, the LV lead 1024, and the right ventricular lead 1030 through the switch 1074 to sample cardiac signals across any pair of desired electrodes. The microcontroller 1060 is further coupled to a memory 1094 by a suitable data/address bus 1096, wherein the programmable operating parameters used by the microcontroller 1060 are stored and modified, as required, in order to customize the operation of pacer/ICD 10 to suit the needs of a particular patient. Such operating parameters define, for example, the amplitude or magnitude, pulse duration, electrode polarity, for both pacing pulses and impedance detection pulses as well as pacing rate, sensitivity, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 1094 through a telemetry circuit 1100 in telemetric communication with the external device 1102, such as a programmer, transtelephonic transceiver or a diagnostic system analyzer. The telemetry circuit 1100 is activated by the microcontroller by a control signal 1106. The telemetry circuit 1100 advantageously allows intracardiac electrograms and status information relating to the operation of pacer/ICD 10 (as contained in the microcontroller 1060 or memory 1094) to be sent to the external device 1102 through an established communication link 1104. Pacer/ICD 10 further includes an accelerometer or other physiologic sensor 1108, commonly referred to as a "rate-responsive" sensor because it is typically used to adjust pacing stimulation rate according to the exercise state of the patient. However, the physiological sensor 1108 may further be used to detect changes in cardiac output, changes in the physiological condition of the heart, or diurnal changes in activity (e.g., detecting sleep and wake states) and to detect arousal from sleep. Accordingly, the microcontroller 1060 responds by adjusting the various pacing parameters (such as rate, AV delay, VV delay, etc.) at which the atrial and ventricular pulse generators, 1070 and 1072, generate stimulation pulses. While shown as being included within pacer/ICD 10, it is to be understood that the physiologic sensor 1108 may also be external to pacer/ICD 10, yet still be implanted within or carried by the patient. A common type of rate responsive sensor is an activity sensor incorporating an accelerometer or a piezoelectric crystal, which is mounted within the housing 1040 of pacer/ICD 10. Other types of physiologic sensors are also known, for example, sensors that sense the oxygen content of blood, respiration rate and/or minute ventilation, pH of blood, ventricular gradient, etc.

The pacer/ICD additionally includes a battery 1110, which provides operating power to all of the circuits shown in FIG. 13. The battery 1110 may vary depending on the capabilities of pacer/ICD 10. If the system only provides low voltage therapy, a lithium iodine or lithium copper fluoride cell typically may be utilized. For pacer/ICD 10, which employs shocking therapy, the battery 1110 should be capable of operating at low current drains for long periods, and then be capable of providing high-current pulses (for capacitor charging) when the patient requires a shock pulse. The battery 1110 should also have a predictable discharge characteristic so that elective replacement time can be detected. Accordingly, appropriate batteries are employed.

As further shown in FIG. 13, pacer/ICD 10 is shown as having an impedance measuring circuit 1112, which is enabled by the microcontroller 1060 via a control signal

1114. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; detecting the opening of heart valves, and measuring values useful for assessing current drain and device longevity, etc. The impedance measuring circuit 1112 is advantageously coupled to the switch 1174 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 1060 further controls a shocking circuit 1116 by way of a control signal 1118. The shocking circuit 1116 generates shocking pulses of low (up to 0.5 joules), moderate (0.5-10 joules) or high energy (11 to 40 joules), as controlled by the microcontroller 1060. Such shocking pulses are applied to the heart of the patient through at least two shocking electrodes, and as shown in this embodiment, selected from the left atrial coil electrode 1028, the RV coil electrode 1036, and/or the SVC coil electrode 1038. The housing 1040 may act as an active electrode in combination with the RV electrode 1036, or as part of a split electrical vector using the SVC coil electrode 1038 or the left atrial coil electrode 1028 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 7-40 joules), delivered asynchronously (since R-waves may be too disorganized), and pertaining exclusively to the treatment of fibrillation. Accordingly, the microcontroller 1060 is capable of controlling the synchronous or asynchronous delivery of the shocking pulses.

An internal warning device 1099 may be provided for generating perceptible warning signals to the patient via vibration, voltage or other methods.

Insofar as pacing optimization is concerned, for an implementation where QuickStim is performed by the device 10, the microcontroller includes an on-board QuickStim controller 1101 operative to control or perform the QuickStim techniques describe above, alone or in combination with an external system. The on-board QuickStim controller includes: a hemodynamic benefit vs. device longevity bias input unit 11103 operative to input (via telemetry circuit 1100) the aforementioned bias or balance value; a hemodynamic benefit assessment system 1105 operative to assess a degree of hemodynamic benefit expected to be achieved using each of a plurality of sets of stimulation control parameters; a device longevity assessment system 1107 operative to assess a degree of device longevity expected to be achieved using each of the plurality of sets of stimulation control parameters; and a "hemodynamic benefit vs. device longevity" stimulation control parameter selection unit 1109 operative to select a particular set of stimulation control parameters based on the degree of hemodynamic benefit and the degree of longevity. Microcontroller 1060 operates as a pacing therapy controller for controlling the delivering stimulation therapy in accordance with the selected set of control parameters. Note that, in examples wherein QuickStim is fully controlled by an external device, the implantable device need not have each of these on-board QuickStim components.

Insofar as sensing optimization is concerned, for an implementation where QuickSense is performed by the device 10, the microcontroller includes an on-board QuickSense controller 1111 operative to control or perform the QuickSense techniques describe above, alone or in combination with an external system. The QuickSense controller includes: a sensing profile input unit 1111 operative to input a profile representative of preferred cardiac signal sensing features; a sensing profile assessment unit 1115 operative to assess an amount by which each set of sensing vectors matches the input profile; a sensing vector selection unit 1117 operative to select a particular set of sensing vectors for use in sensing based on the degree to which each set of sensing vectors matches the input profile; and a profile-based sensing controller 1119 operative to sense of cardiac signals using the selected set of sensing vectors. Note that, in examples wherein QuickSense is fully controlled by an external device, the implantable device need not have each of these on-board QuickSense components.

Note also that, depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using application specific integrated circuits (ASICs) or the like.

In some examples, the device uses hemodynamic response data received from an implanted hemodynamic response monitor 1121, such as a cardiac output monitor, or from an external hemodynamic response monitor 1123. Other external monitors can additionally or alternatively be used.

As noted, at least some of the techniques described herein can be performed by (or under the control of) an external device. For the sake of completeness, a detailed description of an exemplary device programmer will now be provided.

Exemplary External Programmer

Figure 14:
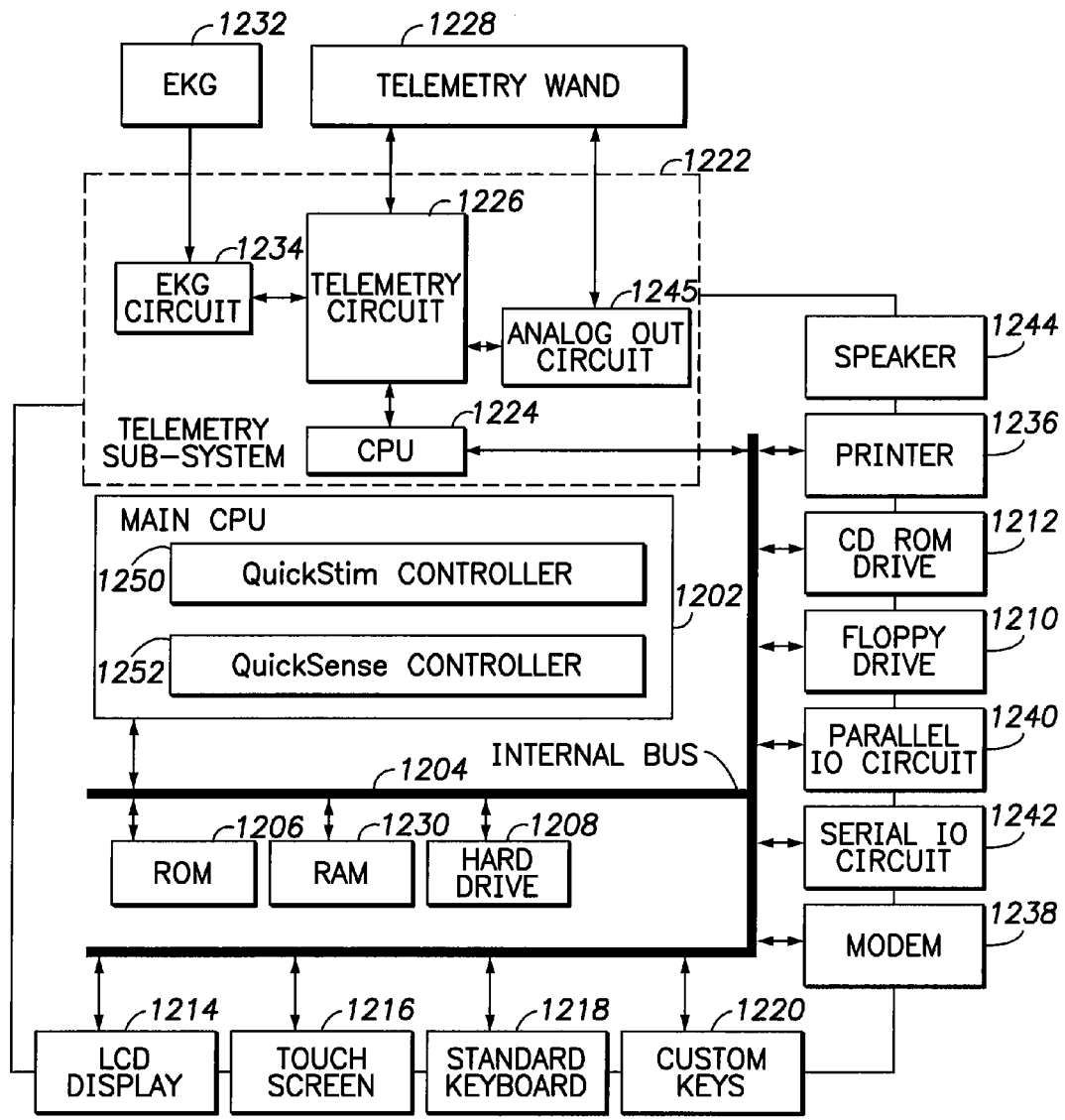
FIG. 14 is a functional block diagram illustrating components of the external device programmer of FIG. 1, particularly illustrating programmer-based systems for performing/controlling the techniques of FIGS. 2-14.

FIG. 14 illustrates pertinent components of an external programmer 14 for use in programming the pacer/ICD of FIGS. 12 and 13 and for performing the above-described optimization techniques. For the sake of completeness, other device programming functions are also described herein. Generally, the programmer permits a physician, clinician or other user to program the operation of the implanted device and to retrieve and display information received from the implanted device such as IEGM data and device diagnostic data. Additionally, the external programmer can be optionally equipped to receive and display electrocardiogram (EKG) data from separate external EKG leads that may be attached to the patient. Depending upon the specific programming of the external programmer, programmer 14 may also be capable of processing and analyzing data received from the implanted device and from the EKG leads to, for example, render preliminary diagnosis as to medical conditions of the patient or to the operations of the implanted device.

Now, considering the components of programmer 14, operations of the programmer are controlled by a CPU 1202, which may be a generally programmable microprocessor or microcontroller or may be a dedicated processing device such as an application specific integrated circuit (ASIC) or the like. Software instructions to be performed by the CPU are accessed via an internal bus 1204 from a read only memory (ROM) 1206 and random access memory 1230. Additional software may be accessed from a hard drive 1208, floppy drive 1210, and CD ROM drive 1212, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 1214 or other suitable computer display device. To this end, the CPU may, for example, display a menu of specific programmable parameters of the implanted device to be programmed or may display a menu of types of diagnostic data to be retrieved and displayed. In response thereto, the physician enters various commands via either a touch screen 1216 overlaid on the LCD display or through a standard keyboard 1218 supplemented by additional custom keys 1220, such as an emergency VVI (EVVI) key. The EVVI key sets the implanted device to a safe VVI mode with high pacing outputs. This ensures life sustaining pacing operation in nearly all situations but by no means is it desirable to leave the implantable device in the EVVI mode at all times.

Once all pacing leads are mounted and the pacing device is implanted, the various parameters are programmed. Typically, the physician initially controls the programmer 14 to retrieve data stored within any implanted devices and to also retrieve EKG data from EKG leads, if any, coupled to the patient. To this end, CPU 1202 transmits appropriate signals to a telemetry subsystem 1222, which provides components for directly interfacing with the implanted devices, and the EKG leads. Telemetry subsystem 1222 includes its own separate CPU 1224 for coordinating the operations of the telemetry subsystem. Main CPU 1202 of programmer communicates with telemetry subsystem CPU 1224 via internal bus 1204. Telemetry subsystem additionally includes a telemetry circuit 1226 connected to telemetry wand 1228, which, in turn, receives and transmits signals electromagnetically from a telemetry unit of the implanted device. The telemetry wand is placed over the chest of the patient near the implanted device to permit reliable transmission of data between the telemetry wand and the implanted device. Herein, the telemetry subsystem is shown as also including an EKG circuit 1234 for receiving surface EKG signals from a surface EKG system 1232. In other implementations, the EKG circuit is not regarded as a portion of the telemetry subsystem but is regarded as a separate component.

Typically, at the beginning of the programming session, the external programming device controls the implanted devices via appropriate signals generated by the telemetry wand to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like. Data retrieved from the pacer/ICD also includes the data stored within the recalibration database of the pacer/ICD (assuming the pacer/ICD is equipped to store that data.) Data retrieved from the implanted devices is stored by external programmer 14 either within a random access memory (RAM) 1230, hard drive 1208 or within a floppy diskette placed within floppy drive 1210. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implanted devices is transferred to programmer 14, the implanted devices may be further controlled to transmit additional data in real time as it is detected by the implanted devices, such as additional IEGM data, lead impedance data, and the like. Additionally, or in the alternative, telemetry subsystem 1222 receives EKG signals from EKG leads 1232 via an EKG processing circuit 1234. As with data retrieved from the implanted device itself, signals received from the EKG leads are stored within one or more of the storage devices of the external programmer. Typically, EKG leads output analog electrical signals representative of the EKG. Accordingly, EKG circuit 1234 includes analog to digital conversion circuitry for converting the signals to digital data appropriate for further processing within the programmer. Depending upon the implementation, the EKG circuit may be configured to convert the analog signals into event record data for ease of processing along with the event record data retrieved from the implanted device. Typically, signals received from the EKG leads are received and processed in real time.

Thus, the programmer receives data both from the implanted devices and from optional external EKG leads. Data retrieved from the implanted devices includes parameters representative of the current programming state of the implanted devices. Under the control of the physician, the external programmer displays the current programmable parameters and permits the physician to reprogram the parameters. To this end, the physician enters appropriate commands via any of the aforementioned input devices and, under control of CPU 1202, the programming commands are converted to specific programmable parameters for transmission to the implanted devices via telemetry wand 1228 to thereby reprogram the implanted devices. Prior to reprogramming specific parameters, the physician may control the external programmer to display any or all of the data retrieved from the implanted devices or from the EKG leads, including displays of EKGs, IEGMs, and statistical patient information. Any or all of the information displayed by programmer may also be printed using a printer 1236.

Programmer/monitor 14 also includes a modem 1238 to permit direct transmission of data to other programmers via the public switched telephone network (PSTN) or other interconnection line, such as a T1 line or fiber optic cable. Depending upon the implementation, the modem may be connected directly to internal bus 1204 may be connected to the internal bus via either a parallel port 1240 or a serial port 1242. Other peripheral devices may be connected to the external programmer via parallel port 1240 or a serial port 1242 as well. Although one of each is shown, a plurality of input output (IO) ports might be provided. A speaker 1244 is included for providing audible tones to the user, such as a warning beep in the event improper input is provided by the physician. Telemetry subsystem 1222 additionally includes an analog output circuit 1245 for controlling the transmission of analog output signals, such as IEGM signals output to an EKG machine or chart recorder.

Insofar as pacing and sensing optimization is concerned, main CPU 1202 includes a QuickStim controller 1250 operative to determine optimal or preferred pacing configurations based using the pacing configuration selection and optimization techniques described above. A selected pacing configuration is then programmed into the implanted device for use therein. The main CPU includes a QuickSense controller 1252 operative to determine optimal or preferred sensing configurations based using the sensing configuration selection and optimization techniques described above. A selected sensing configuration is then programmed into the implanted device for use therein. If the pacer/ICD has on-board QuickStim and QuickSense components, then the QuickStim and QuickSense controllers or the external device may be equipped to operate in conjunction with those on-board components.

Depending upon the implementation, the various components of the CPU may be implemented as separate software modules or the modules may be combined to permit a single module to perform multiple functions. In addition, although shown as being components of the CPU, some or all of these components may be implemented separately, using ASICs or the like.

Note that, in at least some examples, the pacing and sensing optimization components employ information received by the external programmer from external monitoring devices, such as external hemodynamic monitors. Such information can be input via the various input systems already noted, such as the parallel or serial IO circuits.

With the programmer configured as shown, a clinician or other user operating the external programmer is capable of retrieving, processing and displaying a wide range of information received from the implanted device and to reprogram the implanted device if needed.

The descriptions provided herein with respect to FIG. 13 are intended merely to provide an overview of the operation of programmer and are not intended to describe in detail every feature of the hardware and software of the programmer and is not intended to provide an exhaustive list of the functions performed by the programmer.

In general, while the invention has been described with reference to particular embodiments, modifications can be made thereto without departing from the scope of the invention. Note also that the term "including" as used herein is intended to be inclusive, i.e. "including but not limited to."

What is claimed is:

1. A system for use with an implantable cardiac stimulation device equipped to delivery stimulation therapy in accordance with a selectable set of control parameters, the system comprising:
    a hemodynamic benefit assessment system operative to assess a degree of hemodynamic benefit expected to be achieved using each of a plurality of sets of stimulation control parameters;
    a device longevity assessment system operative to assess a degree of device longevity expected to be achieved using each of the plurality of sets of stimulation control parameters;
    a stimulation control parameter determination unit operative to select a particular set of stimulation control parameters based on the degree of hemodynamic benefit and the degree of longevity; and
    a pacing therapy controller operative to control the delivering stimulation therapy in accordance with the determined set of control parameters.

2. A system for use with an implantable cardiac stimulation device equipped to delivery stimulation therapy in accordance with a selectable set of control parameters, the system comprising:
    means for assessing a degree of hemodynamic benefit expected to be achieved using each of a plurality of sets of stimulation control parameters;
    means for assessing a degree of device longevity expected to be achieved using each of the plurality of sets of stimulation control parameters;
    means for determining a particular set of stimulation control parameters based on the degree of hemodynamic benefit and the degree of longevity; and
    means for controlling the delivering stimulation therapy in accordance with the determined set of control parameters.

* * * * *